US008440455B2

(12) United States Patent
Scherman et al.

(10) Patent No.: US 8,440,455 B2
(45) Date of Patent: May 14, 2013

(54) PLASMIC PRODUCTION AND EXPRESSION OF RECOMBINANT PROTEINS IN CELLS GROWN WITHOUT ANTIBIOTICS

(75) Inventors: Daniel Scherman, Paris (FR); Corinne Marie, Yerres (FR)

(73) Assignees: Centre Ntional de la Recherche Scientifique (CNRS), Paris (FR); Universites Paris Descartes Institut National de la Sante et de la Recherche Medicale (Inserm), Paris (FR)

( * ) Notice: Subject to any disclaimer, the term of this patent is extended or adjusted under 35 U.S.C. 154(b) by 142 days.

(21) Appl. No.: 12/675,011

(22) PCT Filed: Aug. 22, 2008

(86) PCT No.: PCT/EP2008/061045
§ 371 (c)(1),
(2), (4) Date: May 10, 2010

(87) PCT Pub. No.: WO2009/027351
PCT Pub. Date: Mar. 5, 2009

(65) Prior Publication Data
US 2011/0129487 A1    Jun. 2, 2011

(30) Foreign Application Priority Data
Aug. 24, 2007 (FR) ..................... 07 57175

(51) Int. Cl.
*C12N 15/00* (2006.01)
(52) U.S. Cl.
USPC ...................... 435/320.1; 435/91.1
(58) Field of Classification Search ................ 435/320.1
See application file for complete search history.

(56) References Cited

U.S. PATENT DOCUMENTS
5,122,458 A * 6/1992 Post et al. ............... 435/69.1
6,689,758 B1 * 2/2004 Braddock et al. .......... 514/44 R

FOREIGN PATENT DOCUMENTS
WO    WO 2004/033664 A2    4/2004

OTHER PUBLICATIONS

Ultracomp *E.coli*; Invitrogen; Apr. 13, 2004.*
pCDM8 Invitrogen; http://tools.invitrogen.com/content/sfs/vectors/pcdm8.pdf; accessed Sep. 17, 2012.*
Gabriel et al.; A Set of Plasmids Constitutively Producing Different RNA Levels in *Escherichia coli*; Journal of Molecular Biology; vol. 290; pp. 385-389; (1999).*
Acsadi et al.; Human dystrophin expression in mdx mice after intramuscular injection of DNA constructs; Nature; vol. 352; pp. 815-818; Sep. 29, 1991.*
pQE-70 vector; Qiagen, http://www.qiagen.com/literature/pqesequences/pqe70.pdf; accessed Sep. 17, 2012.*

International Search Report issued in application No. PCT/EP2008/061045 on Nov. 10, 2008.
French Search Report issued in application No. FR 0757175 on Mar. 5, 2008.
Bauer et al., Human TLR9 confers responsiveness to bacterial DNA via species-specific CpG motif recognition, *PNAS*, vol. 98, No. 16, pp. 9237-9242, Jul. 31, 2001.
Chaung, "CpG oligodeoxynucleotides as DNA adjuvants in vertebrates and their applications in immunotherapy," *International Immunopharmacology*, vol. 6, pp. 1586-1596, 2006.
Bradley et al., "tRNA$_2$$^{Gln}$Su+2 Mutants That Increase Amber Suppression," *Journal of Bacteriology*, vol. 145, No. 2, pp. 704-712, Feb. 1981.
Blattner et al., "The Complete Genome Sequence of *Escherichia coli* K-12," *Science*, vol. 277, pp. 1453-1462, 1997.
Garmory et al, "DNA vaccines: improving expression of antigens," *Genetic Vaccines and Therapy*, vol. 1, No. 2, 2003.
Kreiss et al., "Production of a new DNA vehicle for gene transfer using site-specific recombination," *Appl. Microbiol. Biotechnol.*, vol. 49, pp. 560-567, 1998.
Kleina et al., "Construction of *Escherichia coli* Amber Suppressor tRNA Genes," *J. Mol. Biol.*, vol. 213, pp. 705-717, 1990.
Nakamura et al., "DNA Sequence of the Gene for the Outer Membrane Lipoprotein of *E. coli*: an Extremely AT-Rich Promotor," *Cell*, vol. 18, pp. 1109-1117, Dec. 1979.
Michaels et al., "*Escherichia coli* thymidylate synthase: Amino acid substitutions by suppression of amber nonsense mutations," *Proc. Natl. Acad. Sci.*, vol. 87, pp. 3957-3961, May 1990. Normanly et al., "Construction of two *Escherichia coli* amber suppressor genes: tRNA$^{Phe}_{CUA}$ and tRNA$^{CYS}_{CUA}$," *Proc. Natl. Acad. Sci. USA*, vol. 83, pp. 6548-6552, 1986.
Normanly et al., "Construction of *Escherichia coli* Amber Suppressor tRNA Genes," *J. Mol. Biol.*, vol. 213, pp. 719-726, 1990.
Posfai et al., "Versatile Insertion Plasmids for Targeted Genome Manipulations in Bacteria: Isolation, Deletion, and Rescue of the Pathogenicity Island LEE of the *Escherichia coli* O157:H7 Genome," *Journal of Bacteriology*, vol. 179, No. 13, pp. 4426-4428, 1997.
Posfai et al., "Markerless gene replacement in *Escherichia coli* stimulated by a double-strand break in the chromosome," *Nucleic Acids Research*, vol. 27, No. 22, pp. 4409-4415, 1999.
Chen et al., "Minicircle DNA Vectors Devoid of Bacterial DNA Result in Persistent and High-Level Transgene Expression in Vivo," *Molecular Therapy*, vol. 8, No. 3, pp. 495-500, 2003.

(Continued)

*Primary Examiner* — Michele K Joike
*Assistant Examiner* — Antonio Galisteo Gonzalez
(74) *Attorney, Agent, or Firm* — Foley & Lardner LLP

(57) ABSTRACT

The invention relates to a mutated cell such as a bacteria or yeast in which the thyA gene coding thymidylate synthase includes a nonsense codon, preferably the amber codon, said nonsense codon replacing a codon coding an amino acid and inducing the interruption of thyA gene translation and the auxotrophy of the cell for the thymidine. Advantageously, the endA gene coding the endonuclease 1 and/or the recA gene coding the recombinase is inactivated in said mutated cell. The invention also relates to an expression plasmid including a transgene and a sequence of a suppressing ARM structural gene containing an anticodon that can be paired with the nonsense codon of the thyA gene and is specific of an amino acid capable of restoring the translation of the mutated thyA gene and thereby obtaining a protein of the wild or mutated type having a thymidylate synthase activity. The invention also relates to a method for the multiplication of the expression plasmid.

6 Claims, 13 Drawing Sheets

OTHER PUBLICATIONS

Chen et al., "Improved Production and Purification of Minicircle DNA Vector Free of Plasmid Bacterial Sequences and Capable of Persistent Transgene Expression in Vivo," *Human Gene Therapy*, vol. 16, pp. 126-131, 2005.

Cranenburgh et al., "*Eshcerichia coli* strain that allow antibiotic-free plasmid slection and maintenance by repressor titration," *Nucleic Acids Research*, vol. 29, No. 5, 2001.

Cranenburgh et al., "Effect of Plasmid Copy Number and *lac* Operator Sequence on Antibiotic-Free Plasmid Selection by Operator-Repressor Titration in *Escherichia coli*," *J. Mol., Microbiol. Biotechnol.*, vol. 7, pp. 197-203, 2004.

Schoenfeld et al., "Effects of Bacterial Strains Carrying the *endA1* Genotype on DNa Quality Isolated with Wizard™ Plasmid Purification Systems," *Promega Notes Magazine*, No. 53, p. 12, 1995.

Young, "Transcription Termination in the *Escherichia coli* Ribosomal RNA Operon rrnC*," *The Journal of Biological Chemistry*, vol. 254, No. 24, pp. 12725-12731, 1979.

Singh et al., "Advances in Vaccine Adjuvants for Infectious Diseases," *Current HIV Research*, vol. 1, pp. 309-320, 2003.

Soubrier et al., "pCOR: a new design of plasmid vectors for nonviral gene therapy," *Gene Therapy*, vol. 6, pp. 1482-1488, 1999.

Jiang et al., "In Vitro Assay of Immunostiumlatory Activities of Plasmid Vectors," *Methods in Medicine*, vol. 127, Ed., Saltzman et al., $2^{nd}$ ed., pp. 55-70, 2006.

Demarre et al., "A new family of mobilizable suicide plasmids based on broad host range R388 plasmid (IncW) and RP4 plasmid (IncPα) conjugative machineries and their cognate *Escherichia coli* host strains," *Research in Microbiology*, vol. 156, pp. 245-255, 2005.

He et al., Response of nitric oxide production to CpG oligodeoxynucleotides in turkey and chicken peripheral blood monocytes, *FEMS Immunol. Med. Microbiol.*, vol. 48, pp. 99-106, 2006.

Herring et al., "Conditional Lethal Amber Mutations in Essential *Escherichia coli* Genes," *Journal of Bacteriolgy*, vol. 186, No. 9, pp. 2673-2681, 2004.

Dickely et al., "Isolation of *Lactococcus lactis* nonsense suppressors and construction of a food-grate cloning vector," *Molecular Microbiology*, vol. 15, No. 5, pp. 839-847, 1995.

Kandimalla et al., "Towards optimal design of second-generation immunomodulatory oligonucleotides," *Current Opinion in Molecular Therapeutics*, vol. 4, No. 2, pp. 122-129, 2002.

Patrick Kreiss et al., Plasmid DNA Size Does Not Affect the Physiochemical Properties of Lipoplexes but Modulates Gene Transfer Efficiency, Nucleic Acids Research, 1999, vol. 27, No. 9, pp. 3792-3798.

Maria J. Molnar et al., Factors Influencing the Efficacy, Longevity, and Safety of Electroporation-Assisted Plasmid-Based Gene Transfer into Mouse Muscles, Molecular Therapy, Sep. 2004, vol. 10, No. 3, pp. 447-455.

Wenxuan Yin et al., Investigations of the Effect of DNA Size in Transient Transfection Assay Using Dual Luciferase System, Analytical Biochemistry, 2005, vol. 346, pp. 289-294.

* cited by examiner

Figure 4:
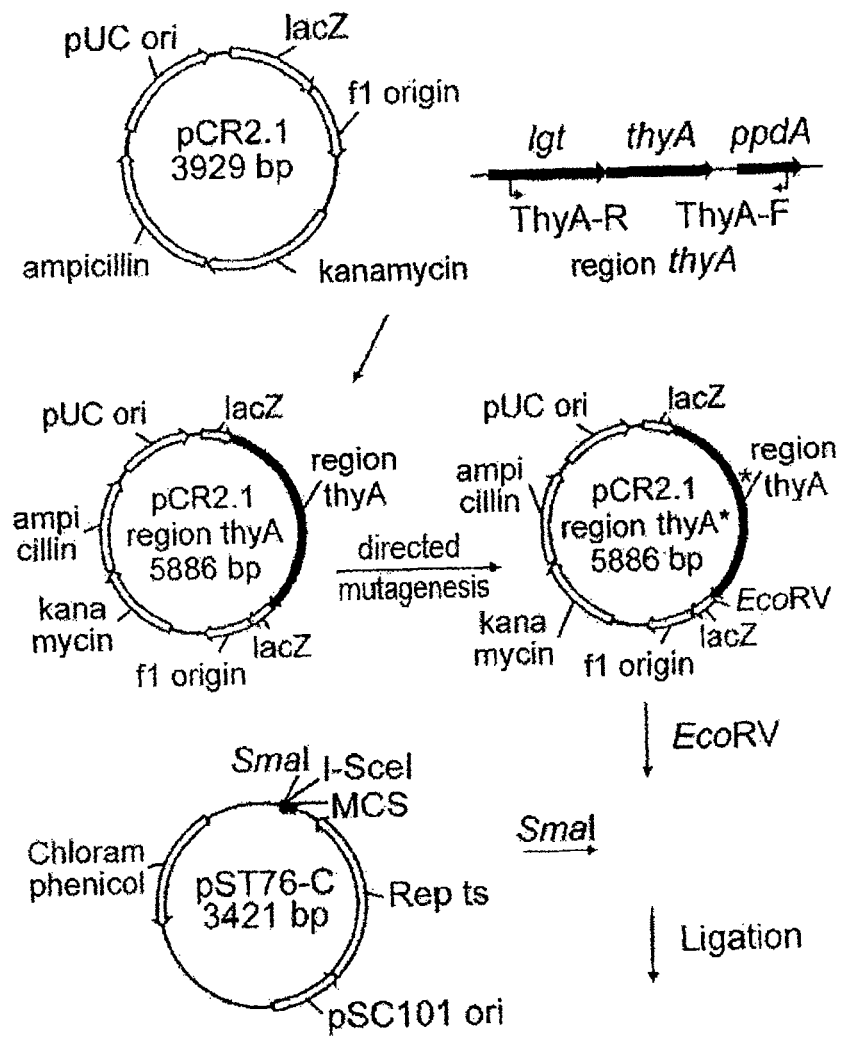

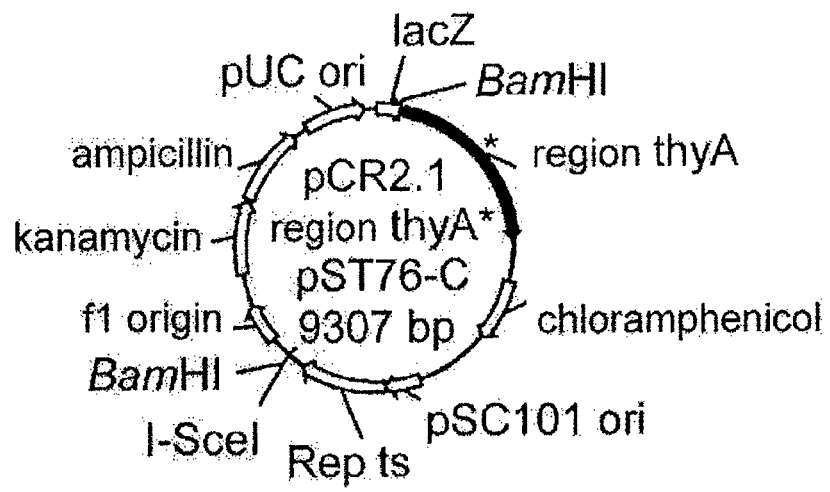
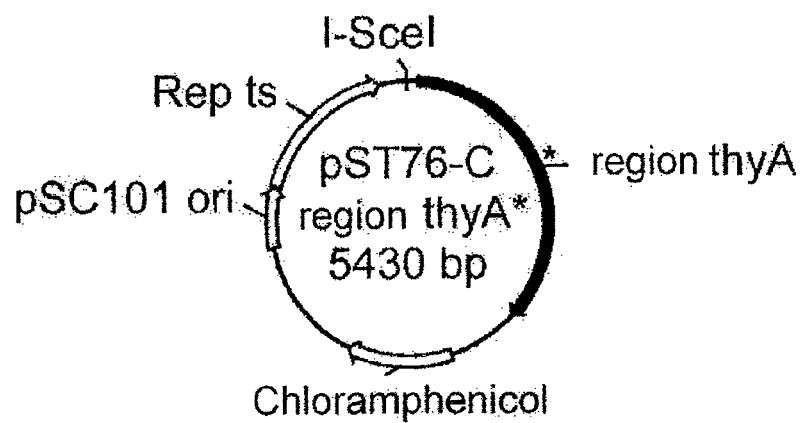
Figure 4 (end)

Figure 5 (end)

Figure 6:
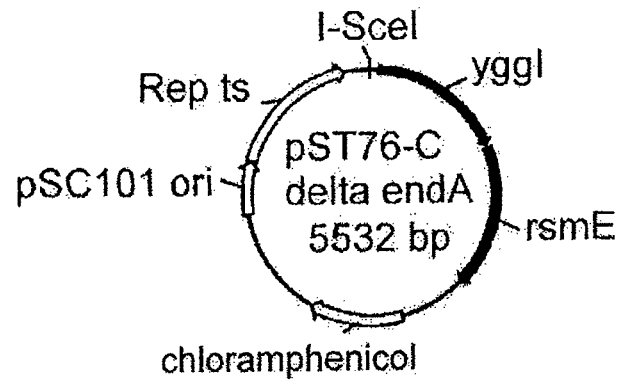
Figure 6:
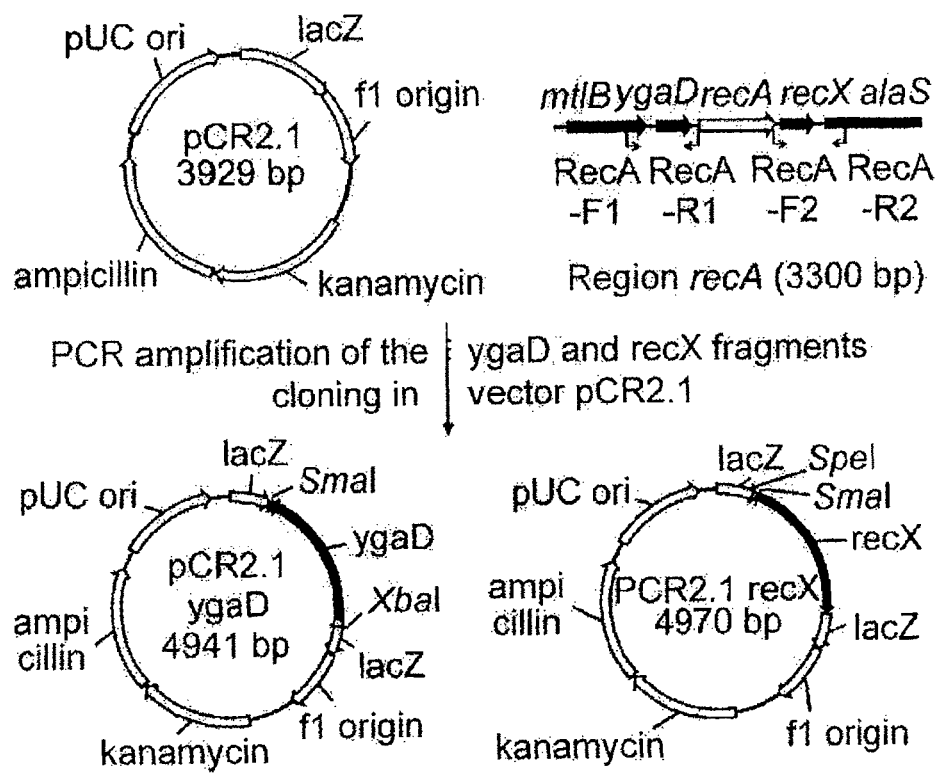
Figure 6:
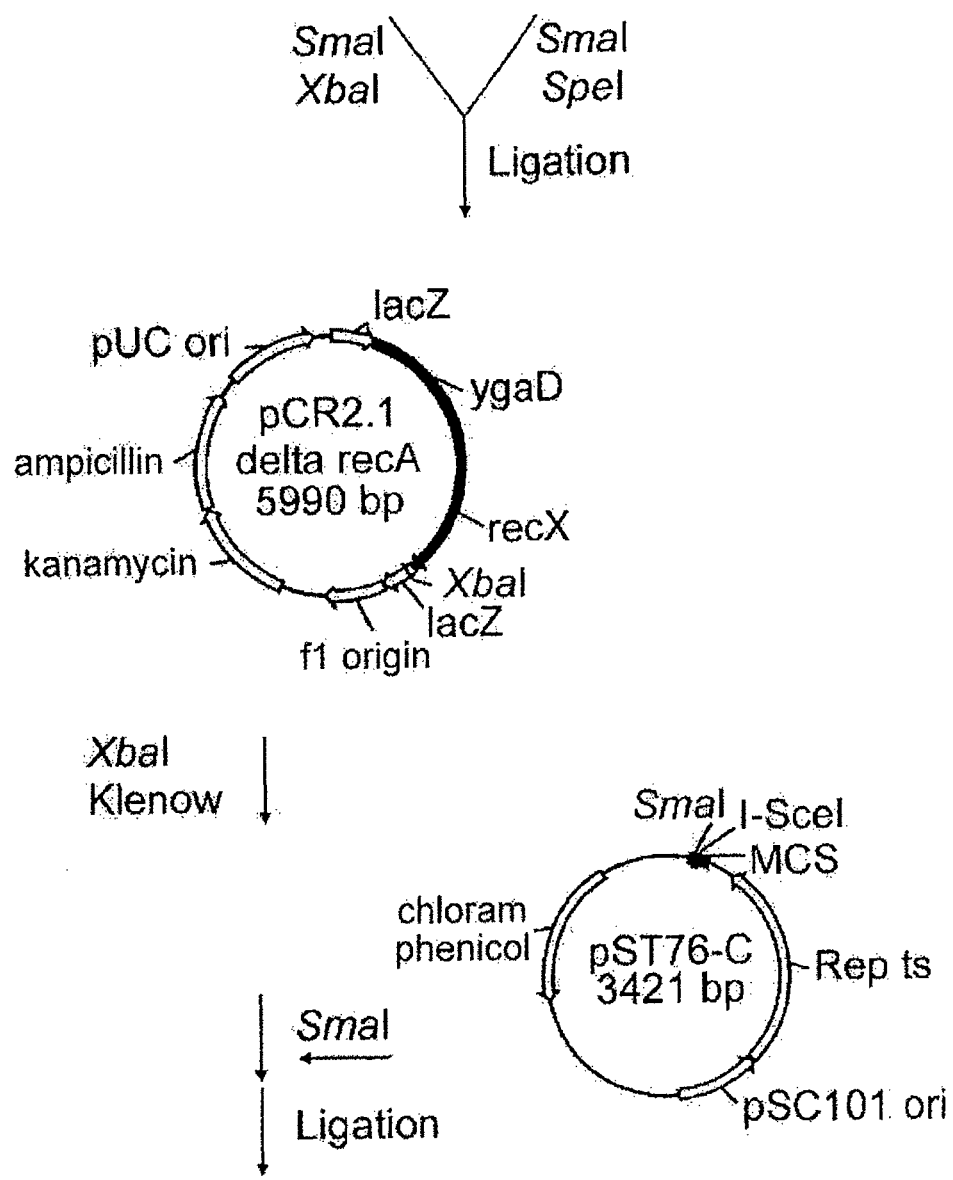

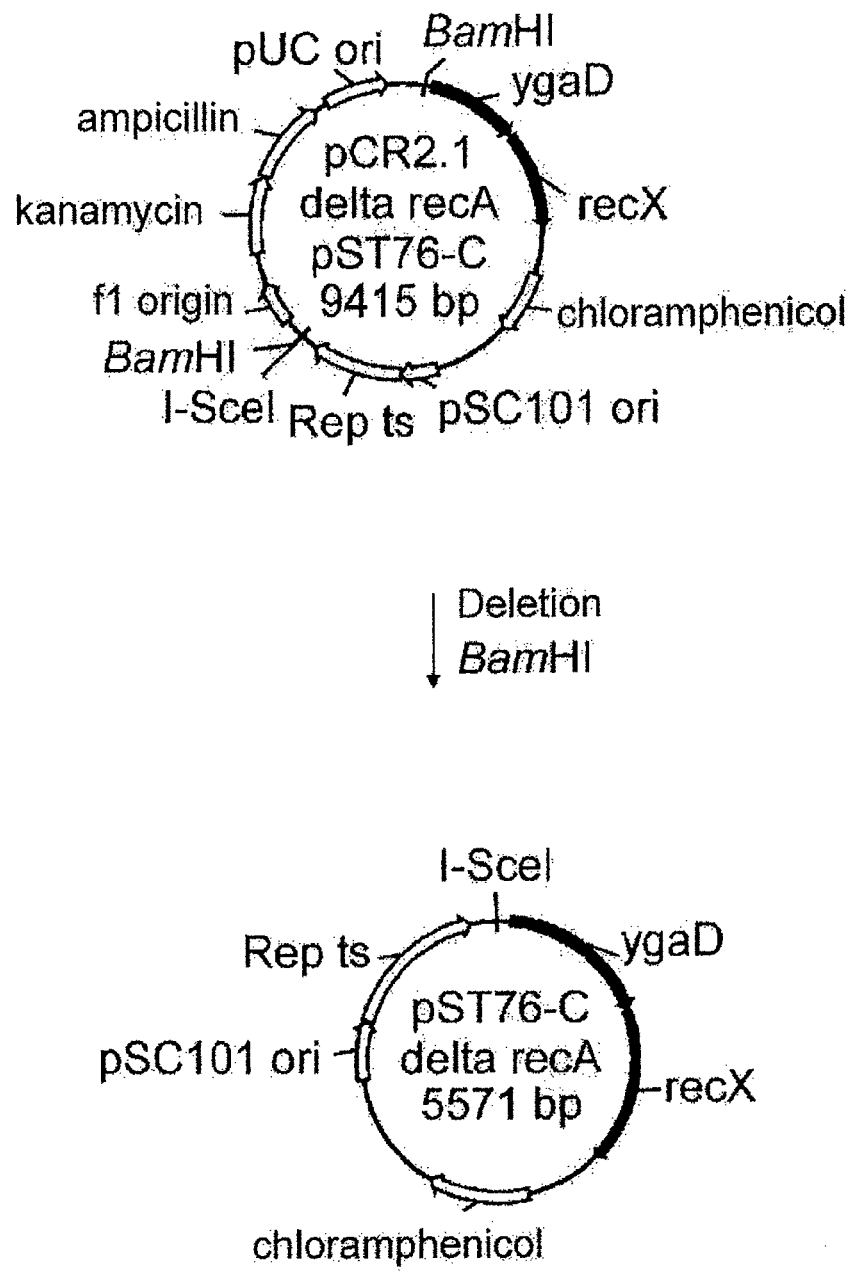
Figure 6 (end)

Figure 7 (end)

PLASMIC PRODUCTION AND EXPRESSION OF RECOMBINANT PROTEINS IN CELLS GROWN WITHOUT ANTIBIOTICS

SEQUENCE LISTING

The instant application contains a Sequence Listing which has been submitted in ASCII format via EFS-Web and is hereby incorporated by reference in its entirety. Said ASCII copy, created on Jan. 13, 2011, is named 65691716.txt and is 10,558 bytes in size.

The present invention relates to a mutated cell such as a bacterium or yeast in which the thyA gene coding for thymidylate synthase includes a nonsense codon, preferably the amber codon, said nonsense codon replacing a codon coding for an amino acid and leading to an interruption of thyA gene translation and auxotrophy of the cell for thymidine. Advantageously, the endA gene coding for endonuclease 1 and/or the recA gene coding for the recombinase is inactivated in said mutated cell. The invention also relates to an expression plasmid comprising a transgene and a sequence of a suppression tRNA structural gene comprising an anticodon which may be paired with the nonsense codon of the thyA gene and which is specific of an amino acid capable of restoring the translation of the mutated thyA gene and thereby obtaining a wild-type or mutated protein having a thymidylate synthase activity. A method for multiplying the expression plasmid is also claimed.

The treatment of diseases or vaccination resorts to the injection of therapeutic or antigenic proteins. The said proteins are generally purified from bacterial cells or other cells such as yeasts which contain expression vectors. Alternatively, the proteins of interest may also be expression in vivo, after injecting the expressed plasmid in human or animal cells. This technique is designated as gene therapy when the expressed protein has a curative aspect and DNA vaccination when the protein of interest is coded by a portion of the genetic material of a pathogenic or toxic agent, thereby triggering a protective immune reaction.

The expression plasmids generally bear a replication origin, a selection gene such as a gene for resistance to an antibiotic (kanamycin, promoting the maintenance of the plasmid in the host cell, and one or more transgenes with sequences required for their expression in animal cells (enhancer, promoter, polyadenylation sequences . . . ), or other cells such as yeasts or bacteria.

The expression plasmids are generally obtained by multiplication in dividing *Escherichia coli* (*E. coli*) bacterial cells. In order to ensure that the plasmids to be isolated or expressing the recombinant proteins are retained in the bacterial cultures, a selection pressure such as resistance to an antibiotic, is exerted. However, within the scope of clinical use, it is not recommended to use plasmids or recombinant proteins which have been prepared from culture media containing antibiotics. The injection of antibiotics may lead to sensitization or to anaphylactic shocks. Further, in vivo, the injected plasmids may be transferred to the microbes of the endogenous and then environmental flora, which may then acquire in this way resistance to antibiotics.

Plasmids without genes for resistance to antibiotics have already been constructed, notably by using a selection system based on a mechanism for titrating a repressor: the essential chromosomal gene dapD (involved in the synthesis of peptidoglycan) of *E. coli* is placed under the transcriptional control of the lac promoter/operator. In the absence of any inducer in the culture medium, the repressor of the lac operon binds to the operator and inhibits the expression of the essential gene. Only the strains which contain a plasmid bearing the operation sequences grow. The presence of this plasmid allows titration of the repressor bound to the operator located upstream from the dapD gene and restoration of the bacterial growth (Cranenburg et al., 2001 and 2004). However it appears that the yield of plasmids prepared by using this strategy is not satisfactory.

Another strategy consists of constructing mini-circles only containing the expression cassette of the eukaryotic gene. The mini-circles are generated in bacteria from a plasmid which bears the prokaryotic sequences required for its propagation and an expression cassette of the eukaryotic gene flanked by sites recognized by a recombinase. The recombination generates two molecules: the mini-circles and a "mini-plasmid" carrying the bacterial sequences (Kreiss et al., 1998). The latter may possibly be digested by using endonucleases (Chen et al., 2003 and 2005). Obtaining mini-circles requires several steps: recombination of the plasmid DNA in order to generate the mini-circles, possible digestion of the mini-plasmids bearing the bacterial DNA and purification of the mini-circles. Although the techniques for purifying and obtaining the mini-circles have been considerably improved, a contamination of the preparations by native plasmids (due to partial recombination) or by mini-plasmids carrying prokaryotic sequences (due to an enzymatic digestion or to incomplete purification) cannot be excluded.

There is therefore a need for finding a new selection system for multiplying expression plasmids without genes for resistance to antibiotics.

This need is met by the present invention, which allows selection of bacteria transformed by the expression plasmid by using a rich medium and obtention of a good yield, may be obtained by resorting to standard purification techniques. In vivo, these plasmids do not have any disadvantage in comparison with currently used expression vectors.

The present invention consists in a novel combination of a mutant strain of *E. coli* and of plasmids without any gene for resistance to antibiotics. The production of these plasmids is based on the suppression of a point-like mutation generating a stop codon (nonsense mutation) introduced in an essential gene of *E. coli*, by a tRNA suppressor coded by the plasmid of interest (cf. FIG. 1).

The fields of use of the present invention are the vectors used for transfecting animal cells, producing vectors for DNA vaccination or gene therapy in humans or animals, and the use of vectors for producing recombinant proteins.

Thus, according to a first aspect, the object of the present invention is a mutated cell in which the thyA gene coding for thymidylate synthase (ThyA) contains a nonsense codon, said nonsense codon replacing a codon coding for an amino acid and leading to the interruption of the translation of the thyA gene and auxotrophy of said cell for thymidine.

The term "mutated cell" is intended to designate any cell expressing the ThyA protein in which a mutation is introduced into the thyA gene (mutated thyA gene). Advantageously, the mutated cell is selected from bacteria and yeasts.

The bacteria or yeasts which may be used within the scope of the present invention may be of any kinds, it being understood that the latter should contain the thyA gene coding for thymidylate synthase (thyA). These are for example yeasts of genus *Pichia* or *Saccharomyces* or bacteria *Escherichia coli* (*E. coli*), *Salmonella*, *Shigella* or *Listeria*. Preferably, the mutated cell according to the invention is an *Escherichia coli* bacterium (*E. coli*). Advantageously, the *E. coli* strain is the MG1655 strain (obtained from "The Coli Genetic Stock Center", USA) for which the genome has been entirely sequenced (Blattner et al., 1997).

The four nucleotide bases of DNA molecules bear the genetic information. This information, in the form of codons of three contiguous bases, is transcribed into mRNA and then translated by tRNA and the ribosomes for forming proteins. The genetic code is the relationship between a codon and a particular amino acid. Among the 64 possible codons which form the genetic code, there are three "stop" codons or nonsense codons or further termination codons, which are known for stopping the production of proteins at the ribosomes. The three stop codons are the amber codon UAG, the ochre codon UAA and the opal codon UGA. The mutations which change a codon into a stop codon are called nonsense mutations and lead to the interruption of protein synthesis.

The amber nonsense mutation is preferred because the stop codons UAG are a minority (7.6%) relatively to the stop codons UAA (63%) and UGA (29.4%). This minimizes the risk of affecting the synthesis of other bacterial proteins by recognition of the stop codon by a suppressor tRNA, causing insertion of an amino acid.

The transfer RNAs (tRNAs) translate mRNA into a protein on the ribosome. Each tRNA contains an anticodon region which hybridizes with mRNA, and an amino acid which may be bound to the protein during synthesis. tRNAs have a size comprised between about 72 and 90 nucleotides and fold back into a "clover leaf" structure. The tRNAs are transcribed by RNA polymerase III and contain their own promoters which become part of the sequence coding for mature tRNA. The nonsense suppressors are alleles of tRNA genes which are modified in the anticodon so that they may insert an amino acid by hybridizing to a stop codon. For example, an amber mutation in a gene results in the creation of an UAG codon in the mRNA. A suppressor gene of the amber mutation produces a tRNA with a CUA anticodon which introduces an amino acid at the UAG site, so that the translation may continue in spite of the presence of the amber termination codon.

The lethal nonsense mutation is introduced into the thyA gene which codes for thymidylate synthase (thyA) (EC 2.1.1.45). This enzyme is involved in the synthesis of deoxythymidine 5'-monophosphate (dTMP), a precursor used during the DNA synthesis. The nonsense mutation may also be introduced into the thyA gene coding for a protein having the enzymatic properties of thymidylate synthase (EC 2.1.1.45).

The obtained mutants are auxotrophic for thymidine and are isolated by adding this supplement in the culture medium. Thymidine penetrates the cells via a nucleoside transporter and is then transformed into dTMP through an alternative route involving thymidine kinase (cf. FIG. 2). In the absence of exogenous supply of thymidine, the mutation in the thyA gene is lethal; only the strains which contain a plasmid bearing a replication origin, a specific expression cassette of mammal cells, bacteria, yeasts or other cells, and a suppressor tRNA, grow. The latter contains a modified anticodon so as to allow pairing with the stop codon, thereby restoring a complete translation of the ThyA protein of the wild or mutated type but nevertheless having thymidylate synthase enzymatic activity. The strains bearing the plasmid are therefore selected by restoration of their growth. This selection does not require the use of antibiotics and may be performed by using a rich medium such as the one of Mueller Hinton containing tiny or even zero amounts of thymidine (Fluka).

The nonsense mutation may be introduced in any site of the thyA gene, in positions where suppression by the suppressor tRNA will be effective. Many studies have actually shown that the nucleic sequence localized downstream from the amber mutation has an influence on the suppression efficiency (Kleina et al., 1990; Normanly et al., 1986). Preferably, the mutated *Escherichia coli* (*E. coli*) bacteria is characterized in that the nonsense codon replaces a codon coding for an amino acid of thymidylate synthase selected from the group formed by histidine in position 147, glutamate in position 14 or 223, arginine in position 35 or 127, phenylalanine in position 30, aspartate in position 81 or 105, glutamine in position 33 and asparagine in position 121. In a more preferred way, the nonsense codon replaces the codon coding for histidine in position 147 of thymidylate synthase.

The nonsense UAG mutations are preferentially suppressed by using suppressor tRNAs of the Phe, Cyst, His, Gly, Ala, Lys, Pro or Gln type which are effective suppressors of amber mutation and/or by inserting the desired amino acid (Bradley et al., 1981; Normanly et al., 1986 and 1990; Kleina et al., 1990). Modification of the anticodon may actually alter the specificity of the amino acid grafted on tRNA; this is not desirable when the amino acid is present in an active site of the enzyme.

The nonsense mutation introduced at the histidine 147 is efficiently suppressed by using a histidine suppressor tRNA containing a modified anticodon of the CUA type and downstream AA nucleotides; which allow an increase in the suppression efficiency (Kleina et al., 1990).

According to a particular embodiment, the mutated cell according to the invention is characterized in that the nonsense codon is the amber codon UAG.

According to a preferred embodiment, the mutated cell according to the invention is the *E. coli* cell MG1655 thyA#d2 deposited at the Collection Nationale de Cultures de Microorganismes (CNCM), Institut Pasteur, 25 rue du Docteur Roux, 75724 PARIS Cedex 15, France, on Apr. 5$^{th}$ 2007 under the number 1-3739.

Preferably, the mutated cell according to the invention is characterized in that the gene endA coding for endonuclease 1 comprises a mutation inducing better plasmid stability in said mutated cell. Such a cell therefore contains the gene thyA containing a nonsense mutation and the gene endA containing a mutation inducing better plasmid stability.

The quality of plasmid DNA isolated from endA+ strains or endA mutants has been studied (Schoenfeld et al., 1995). It was demonstrated that the quality of DNA prepared from endA mutants is globally better than that of DNA produced in tested endA+ strains.

The mutation may be introduced into the endA gene coding for a protein having the enzymatic properties of endonuclease 1 (EC 3.1.21.1).

The endA gene may be inactivated by mutation such as a deletion, a point-like mutation or an insertion, leading to a loss of the function of the targeted protein. Preferably, the mutation is non-polar; it does not affect the transcription and translation of the genes located downstream from the endA gene. A deletion of the coding sequence is preferred in order to avoid possible reversion events. In a more preferred way, the mutation generates a deletion of the sequence coding for the amino acids 7-234 of the protein EndA which consists of 235 amino acids.

According to a more preferred embodiment, the mutated cell according to the invention is the *E. coli* cell MG1655 thyA endA#1.2.C.3 deposited at the Collection Nationale de Cultures de Microorganismes (CNCM), Institut Pasteur, 25 rue du Docteur Roux, 75724 PARIS Cedex 15, France, on Apr. 5$^{th}$ 2007 under number I-3738.

Preferably, the mutated cell according to the invention is characterized in that the gene recA coding for a recombinase involved in the recombination of DNA sequences is mutated in order to avoid recombination mechanisms between the bacterial genome and the plasmids and between the plasmids. Such a cell therefore contains the gene thyA containing a nonsense mutation, the gene endA containing a mutation inducing better plasmid stability and/or the gene recA containing a mutation for avoiding the recombination mechanisms between the bacterial genome and the plasmids and between the plasmids.

The mutation may be introduced into the recA gene coding for a protein having the enzymatic properties of the recombinase.

The recA gene may be inactivated by mutation such as a deletion, point-like mutation, an insertion leading to a loss of function of the targeted protein. Preferably, the mutation is non-polar; it does not affect the transcription and translation of the genes located downstream from the recA gene. A deletion of the coding sequence is preferred in order to avoid possible reversion events. In a more preferred way, the mutation generates a deletion of the sequence coding for the amino acids 5-343 of the RecA protein which consists of 353 amino acids.

According to a particularly preferred embodiment, the mutated cell according to the invention is the *E. coli* cell MG1655 thyA endA recA#TM1a deposited at the Collection Nationale de Cultures de Microorganismes (CNCM), Institut Pasteur, 25 rue du Docteur Roux, 75724 PARIS Cedex 15, France, on Apr. 5$^{th}$ 2007 under number I-3737.

According to a preferential embodiment, the mutated cell according to the invention is transformed by an expression plasmid and this plasmid comprises:
  a replication origin,
  a nucleotide sequence coding for a recombinant protein of interest,
  an expression cassette for expression of said recombinant protein of interest in a host cell, and
  a structural gene sequence of a suppressor tRNA, said suppressor tRNA comprising an anticodon capable of pairing with a nonsense codon and being specific of an amino acid capable of restoring the translation of said mutated thyA gene in the cell,
  said cell being capable of multiplying in a medium free of thymidine.

The host cell in which is expressed the recombinant protein of interest may be the actual mutated cell or another cell such as a mammalian (human, animal, cell which will be transformed by the expression plasmid according to the invention.

Advantageously, the expression cassette is selected from eukaryotic expression cassettes for expressing said recombinant protein of interest in a mammalian host cell or in a yeast and the prokaryotic expression cassettes for expressing said protein in prokaryotic host cells such as bacterial cells.

The preferred replication origins are those well known to one skilled in the art which lead to the obtaining of several hundred copies of plasmids per cells. The more preferred replication origins are of the ColE1 or pMB1 type or derivatives. In addition to the replication origin which allows initiation of the replication, the expression plasmid contains an eukaryotic or prokaryotic expression cassette allowing expression of the protein of interest in an animal cell, a yeast, a bacteria or other cells. The prokaryotic expression cassettes contain a strong promoter of the type T7, Tac (a hybrid promoter consisting of the region −35 of the promoter trp and of the region −10 of the lacUV5 promoter/operator) or lac. They may also contain labels of the "His", "glutathione S-transferase" or "MBP=maltose binding protein" type intended for purifying the proteins as fusion proteins. A specific site recognized by the proteases of the thrombin, TEV or enterokinase type, may be introduced between the label protein, and the protein of interest, in order to obtain after digestion of the fusion protein, a native protein.

The eukaryotic expression cassettes generally contain a region promoting functional transcription in the animal cell (or promoter), an enhancer (short DNA region on which an activator of transcription may be fixed) and a region located in 3', which specifies a signal of end of transcription and a polyadenylation site (Garmory et al., 2003). Among the different promoters which may be used, mention may be made of: the "immediate-early" ubiquitary promoter/enhancer of the cytomegalovirus CMV. The introduction of an intron downstream from the promoter, such as the intron A, may give the possibility of increasing the expression levels by apparently increasing the polyadenylation rate and/or the nuclear transport associated with splicing of the RNA.

In the case of an application in the fields of gene therapy, immune responses related to an expression in an aberrant site of the product of the transgene may be reduced by using specific promoters of certain tissues such as muscle or skin. Among the specific promoters of muscle, mention may be made of the desmin promoter which controls the expression of the desmin protein specifically localized in muscle filaments, the promoter of muscular creatine kinase which is involved in the transfer of the phosphoryl radical of phosphocreatine towards ADP in order to convert it into ATP. The promoters of genes coding for specific proteins of keratinocytes, cells of the surface layer of the skin, may be used.

The preferred polyadenylation sequences are those of bovine growth hormone, rabbit β-globin or the polyadenylation sequence SV40 possibly in combination with a second enhancer SV40 localized downstream from the polyadenylation signal.

The plasmid may further include adjuvant sequences such as those recognized by the miRNAs (micro RNAs) with which the specificity of cell expression may be improved.

The term of recombinant protein of interest is intended to designate all proteins, polypeptides or peptides, capable of being used in fields such as that of human or animal health, cosmetology, animal nutrition, agro-industry or chemical industry. Advantageously, the recombinant protein of interest is selected from the group formed by the proteins of the eukaryotic type such as those having a therapeutic advantage or those modulating (stimulation/repression) the immune response. Within the scope of DNA vaccination, the protein of interest will belong to the group formed by the antigenic determinants identified in pathogenic agents of humans or animals and possible producing toxins. As examples of recombinant proteins of interest, mention may be made, without however being limited thereto, erythropoietin, dystrophin, insulin, anti-TNFalpha, cytokines, coagulation factors such as the human factor IX, protective antigens such as those from *Bacillus anthracis, Mycobarcterium tuberculosis* and prostate specific membrane antigen (PSMA).

Advantageously, the mutated cell according to the invention is characterized in that the suppressor tRNA is specific for histidine and allows restoration of the translation of the mutated gene thyA which comprises a nonsense codon replacing the codon coding for histidine in position 147 of thymidylate synthase.

Still more advantageously, the mutated cell according to the invention is characterized in that the suppressor tRNA comprises a CUA anticodon capable of being associated with the nonsense amber codon UAG.

Preferably, the mutated cell according to the invention is characterized in that the eukaryotic expression cassette comprises a promoter and polyadenylation sequences, said promoter and said sequences being specific to the host mammalian cells. In a more preferred way, the promoter is the promoter of the cytomegalovirus (CMV) and the polyadenylation sequences are those of the "bovine growth hormone" (BGH).

Also, the expression plasmid contains any element allowing expression of the suppressor tRNA. Advantageously, the mutated cell according to the invention is characterized in that the sequence of the suppressor tRNA structural gene is expressed from a strong promoter lpp of the prokaryotic type (Nakamura et al., 1979) and contains at its end 3' the transcription termination sequence of the operon rrnC (Young, 1979), said sequence being preferably oriented in a divergent way relatively to the nucleotide sequence coding for a recombinant protein of interest. This divergent orientation allows elimination of the risk of expression of the suppressor tRNA from the eukaryotic promoter in host mammal or yeast cells.

Figure 7:
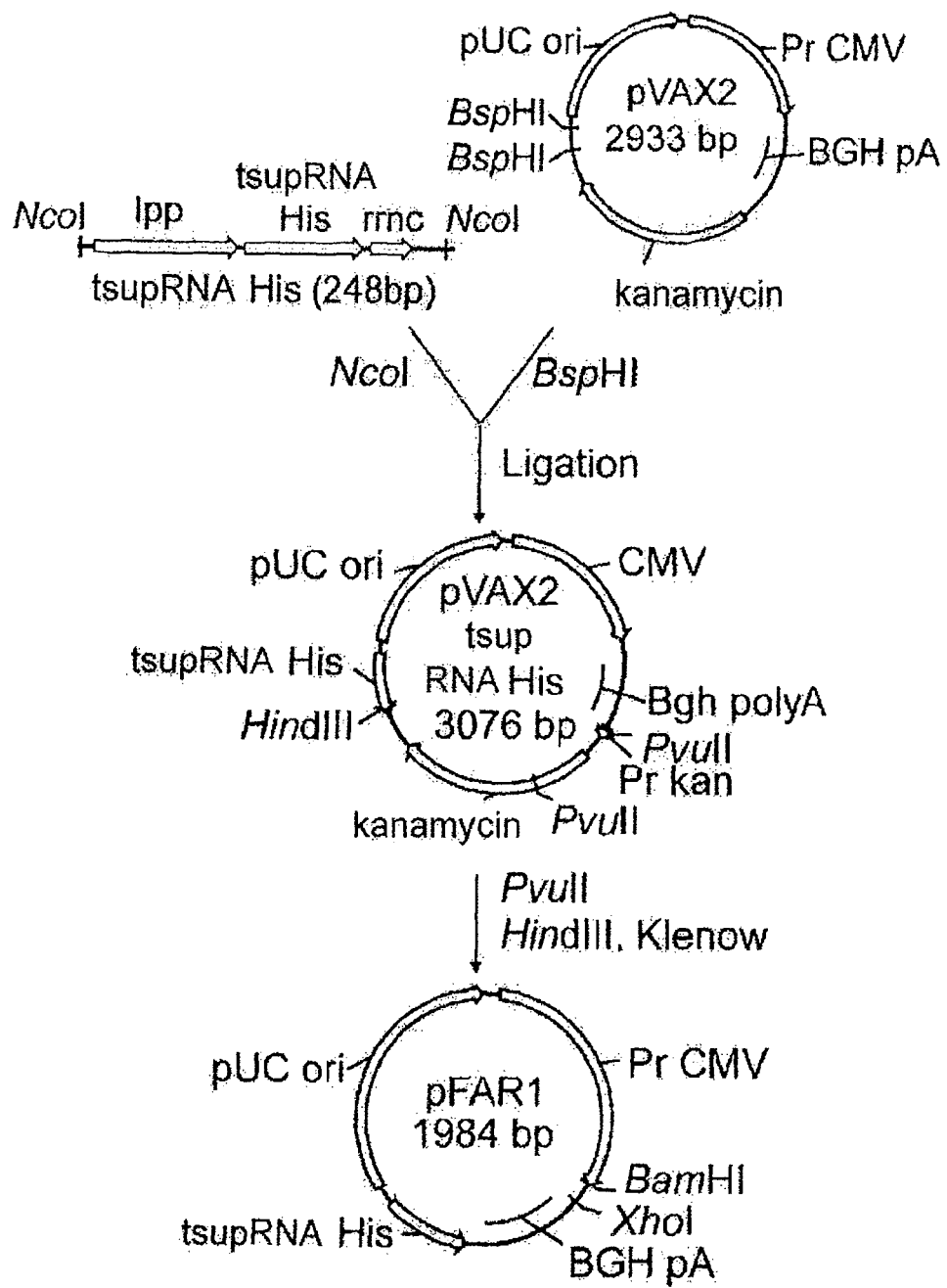

In a more preferred way, the mutated cell according to the invention is characterized in that said plasmid is the plasmid pFAR1 (cf. FIG. 7).

In a way preferred among others, the mutated cell according to the invention is characterized in that said plasmid is the pFAR4 plasmid of sequence SEQ ID NO 21.

Plasmids derived from pFAR4 also form an advantageous embodiment of the invention.

The expression plasmid according to the present invention advantageously has a reduced number of CpG units, which are non-methylated sequences consisting of at least adjacent cytosine and guanine. Such units are known as being responsible for inflammatory and immune responses, which should be avoided in applications of gene therapy. Conversely, an increased immune response is desired in the case of vaccination by administration of DNA coding for an antigen.

DNA vaccines are generally circular plasmids which contain a gene which codes for an antigen placed under the control of an active promoter region in cells of mammals. The expressed protein is then cleaved into peptides which interact with molecules of the histocompatibility complex of class 1, in order to lead to stimulation of the CD8+ lymphocytes.

The immune system also recognizes non-methylated CpG units of bacterial and plasmid DNA. Bacterial DNA differs from that of mammals by the frequency of CpG dinucleotides; the latter being about four times lower in vertebrates. Further, 80% of the CpGs of the DNA of mammals are methylated whereas bacterial DNA is not methylated. These differences cause the immune system to recognize non-methylated CpG units as a danger signal indicating infection by a pathogen. Bacterial DNA and oligonucleotides containing CpG stimulate human and murine leukocytes, inducing proliferation of B cells and secretion of immunoglobulins, activation of macrophages and dendritic cells as well as lysis activity of NK "Natural Killer" cells (Chaung, 2006).

The CpG units may therefore be considered as adjuvants of the DNA type with which the antigenic response of the DNA vaccine may be improved. In the present invention, the CpG units were thereby introduced into the plasmid backbone of the expression vector pFAR4 for the DNA vaccination, pFAR4 then coding for an antigen.

The most immunostimulating CpG units consist of hexanucleotides, the sequence of which is of the Purine-Purine-CpG-Pyrimidine-Pyrimidine type (G/A G/A CG T/C T/C, SEQ ID NO 22). By introducing these sequences into the pFAR4.0, it is therefore possible to obtain enhanced immune response.

Thus, according to a preferred embodiment, the recombinant protein of interest coded by said plasmid is a protective antigen and the expression plasmid contains at least one additional immunostimulating CpG unit, advantageously at least two additional immunostimulating units, even more advantageously between 3 and 10 additional immunostimulating CpG units and, preferably above all, between 3 and 6 additional immunostimulating CpG units.

"An additional immunostimulating CpG unit" is meant to designate in the present invention a CpG unit, i.e. a non-methylated sequence consisting of at least one cytosine and one adjacent guanine, which is introduced into the expression plasmid, unlike the CpG units already present in said plasmid.

Advantageously, these additional immunostimulating CpG units are introduced upstream from the replication origin, preferably between the replication origin and the sequence of suppressor tRNA structural gene. Preferably, the additional immunostimulating CpG unit contains between 2 and 20 nucleotides, preferably between 3 and 10 nucleotides, still more preferably between 4 and 8 nucleotides; most preferably, the additional immunostimulating CpG unit contains 6 nucleotides.

Preferably, the sequence of the additional immunostimulating CpG unit is the hexanucleotide sequence of the type Purine-Purine-C-G-Pyrimidine-Pyrimidine SEQ ID NO. 22). Still preferably, this sequence is selected from the sequences SEQ ID NOs. 23 to 38.

According to a particularly preferred embodiment, the expression plasmid according to the invention contains 6 additional immunostimulating CpG units oriented in the same direction 5'-3' than that of the replication origin, said units being present upstream from the replication origin, preferably between the replication origin and the suppressor tRNA sequence, and the sequences of these 6 units are selected from the sequences SEQ ID NO. 26, SEQ ID NO. 27, SEQ ID NO. 28, SEQ ID NO. 31 and SEQ ID NO. 35.

Advantageously, the 6 sequences corresponding to these units are present in the following order: SEQ ID NO. 28, SEQ ID NO. 2128, SEQ ID NO. 27, SEQ ID NO. 35, SEQ ID NO. 31 and SEQ ID NO. 26 in the 5'-3' orientation as indicated above. An example of such a plasmid is the pFAR5 plasmid (cf. point 8 of the Examples section and FIG. 10B).

According to another particularly preferred embodiment, the expression plasmid according to the invention contains three additional immunostimulating CpG units oriented in the same direction 5'-3' as that of the replication origin, said three units being present upstream of the replication origin, preferably between the replication origin and the suppressor tRNA sequence, and the sequence of these three units is SEQ ID NO. 35. An example of such plasmid is the pFAR6 plasmid (cf. point 8 of the Examples section and FIG. 10C).

Also, the plasmid according to the invention advantageously has a reduced size, a maximum of prokaryotic sequences is eliminated and/or single cloning sites which facilitate molecular manipulations are introduced.

According to a second aspect, the object of the present invention is an expression plasmid comprising a replication origin, a nucleotide sequence coding for a recombinant protein of interest, and expression cassette for expressing said recombinant protein of interest in a host cell and suppressor tRNA structural gene sequence, characterized in that said suppressor tRNA comprises an anticodon capable of pairing with a nonsense codon and is specific of an amino acid capable of restoring translation of the thyA gene in a mutated cell according to the present invention.

Advantageously, the expression cassette is selected from eukaryotic expression cassettes for expressing said recombinant protein of interest in a mammal host cell or in a yeast, and the prokaryotic expression cassettes for expressing said protein in prokaryotic host cells such as bacterial cells.

Preferably, when the mutated cell is *E. coli*, the nonsense codon replaces a codon coding for an amino acid of thymidylate synthase selected from the group formed by histidine in position 147, glutamate in position 14 or 223, arginine in position 35 or 127, phenylalanine in position 30, aspartate in position 81 or 105, glutamine in position 33 and asparagine in position 121. In a more preferred way, the expression plasmid according to the invention is characterized in that the suppressor tRNA is specific of histidine and allows restoration of the translation of the thyA gene including a nonsense codon replacing the codon coding for histidine in position 147 of thymidylate synthase.

Preferably, the suppressor tRNA comprises an anti-codon CUA capable of being associated with the nonsense amber codon UAG.

Preferably, the mutated cell according to the invention is the E. coli cell MG1655 thyA#d2 deposited at the CNCM on Apr. 5$^{th}$ 2007 under number I-3739.

According to a preferred embodiment, the expression plasmid according to the invention is characterized in that the gene endA coding for endonuclease 1 comprises a mutation inducing better plasmid stability in said mutated cell. In a more preferred way, the mutated cell according to the invention is the E. coli cell MG1655 thyA endA#1.2.C.3 deposited on Apr. 5$^{th}$ 2007 at the CNCM under number I-3738.

According to another preferred embodiment, the expression plasmid according to the invention is characterized in that the gene recA coding for a recombinase involved in the recombination of DNA sequences is mutated in order to avoid recombination mechanisms between the bacterial genome and the plasmids and between the plasmids. Still more preferably, the mutated cell according to the invention is the E. coli cell MG1655 thyA endA recA#TM1a deposited on Apr. 5$^{th}$ 2007 at the CNCM under number I-3737.

According to an advantageous embodiment, the expression plasmid according to the invention is characterized in that the eukaryotic expression cassette comprises a promoter and polyadenylation sequences, said promoter and said sequences being specific to mammal host cells. Preferably, the promoter is the promoter of the cytomegalovirus (CMV) and the polyadenylation sequences are of the "bovine growth hormone" (BGH) type.

According to a particularly advantageous embodiment, when the mutated cell is E. coli, the expression plasmid according to the invention is characterized in that the suppressor tRNA structural gene sequence is expressed from the strong promoter lpp of the prokaryotic type and contains at its end 3' the termination sequence of the transcription of the operon rrnC, said sequence being preferably oriented in a divergent way relatively to the nucleotide sequence coding for a recombinant protein of interest.

Still preferably, said expression plasmid is the plasmid pFAR1. Preferably above all, said expression plasmid is the plasmid pFAR4 of sequence SEQ ID NO. 21 or derivatives of pFAR4.

Advantageously, the recombinant protein of interest is selected from the group formed by the proteins of the eukaryotic type such as those having a therapeutic advantage or those modulating (stimulation/repression) the immune response. Within the scope of DNA vaccination, the protein of interest will belong to the group formed by antigenic determinants identified in pathogens of humans or animals, possibly producing toxins. Preferably, the recombinant protein of interest is selected from the group formed by erythropoietin, dystrophin, insulin, anti-TNFalpha, cytokines, coagulation factors such as the human factor IX, protective antigens such as those of Bacillus anthracis, Mycobacterium tuberculosis and the prostate specific membrane antigen (PSMA).

Thus, according to a preferred embodiment, the recombinant protein of interest coded by said plasmid is a protective antigen and the expression plasmid contains at least one additional immunostimulating CpG unit, advantageously at least two additional immunostimulating units, even more advantageously between 3 and 10 additional immunostimulating CpG units and, preferably above all, between 3 and 6 additional immunostimulating CpG units.

Advantageously, these additional immunostimulating CpG units are introduced upstream of the replication origin, preferably between the replication origin and the suppressor tRNA structural gene sequence. Preferably, the additional immunostimulating CpG unit contains between 2 and 20 nucleotides, preferably between 3 and 10 nucleotides, still preferably between 4 and 8 nucleotides; preferably above all, the additional immunostimulating CpG unit contains 6 nucleotides.

Preferably, the sequence of the additional immunostimulating CpG unit is the hexanucleotide sequence of the type Purine-Purine-CpG-Pyrimidine-Pyrimidine (SEQ ID NO. 22). Still preferably, this sequence is selected from the sequences SEQ ID NOs. 23 to 38.

According to a particularly preferred embodiment, the expression plasmid according to the invention contains 6 additional immunostimulating CpG units oriented in the same direction 5'-3' than that of the replication origin, said units being present upstream of the replication origin, preferably between the replication origin and the suppressor tRNA sequence, and the sequences of these 6 units are selected from the sequences SEQ ID NO. 26, SEQ ID NO. 27, SEQ ID NO. 28, SEQ ID NO. 31 and SEQ ID NO. 35.

Advantageously, the 6 sequences corresponding to these units are present in the following order: SEQ ID NO. 28, SEQ ID NO. 28, SEQ ID NO. 27, SEQ ID NO. 35, SEQ ID NO. 31 and SEQ ID NO. 26 in the orientation 5'-3' as indicated above. An example of such a plasmid is the plasmid pFAR5 (cf. point 8 of the Examples section and FIG. 10B).

According to another particularly preferred embodiment, the expression plasmid according to the invention contains three additional immunostimulating CpG units oriented in the same direction 5'-3' as that of the replication origin, said three units being present upstream of the replication origin, preferably between the replication origin and the suppressor tRNA sequence, and the sequence of these three units is SEQ ID NO. 35. An example of such a plasmid is the plasmid pFAR6 (cf. point 8 of the Examples section and FIG. 10C).

According to a third aspect, the object of the present invention is a method for multiplication of an expression plasmid comprising a replication origin, a nucleotide sequence coding for a recombinant protein of interest, and expression cassette for expressing said recombinant protein of interest in a host cell and a sequence of suppressor tRNA structural gene, said method comprising:
  cultivation of a mutated cell in which the gene thyA includes a nonsense codon, said nonsense codon replacing a codon coding for an amino acid and inducing interruption of the translation of the thyA gene and auxotrophy of the mutated cell for thymidine,
  the introduction of the expression plasmid into said grown cell, in which the suppressor tRNA of the expression plasmid comprises an anticodon capable of pairing with the nonsense codon of the thyA gene and is specific of an amino acid capable of restoring the translation of said thyA gene in the mutated cell, and
  the extraction of the expression plasmid from the cell culture, said cultivation being carried out in a medium free of thymidine so as to allow selection of the transformed cells by said expression plasmid.

Advantageously, the expression cassette is selected from the eukaryotic expression cassettes for expressing said recombinant protein of interest in a mammal host cell or in a yeast, and the prokaryotic expression cassettes for expressing said protein in prokaryotic host cells such as bacterial cells.

The introduction of the expression plasmid in the mutated cell may be carried out according to any technique known to one skilled in the art. This may notably be transformation, electroporation, conjugation or any other suitable technique.

The expression plasmids obtained after multiplication are extracted according to any technique known to one skilled in the art.

Preferably, when the mutated cell is *E. coli*, the nonsense codon replaces a codon coding for an amino acid of thymidylate synthase selected from the group formed by histidine in position 147, glutamate in position 14 or 223, arginine in position 35 or 127, phenylalanine in position 30, aspartate in position 81 or 105, glutamine in position 33 and asparagine in position 121. In a more preferred way, the multiplication method according to the invention is characterized in that the suppressor tRNA is specific of histidine and allows restoration of the translation of the thyA gene including a nonsense codon replacing the codon coding for histidine in position 147 of the thymidylate synthase.

In a more preferred way, the method according to the invention is characterized in that the suppressor tRNA comprises an anticodon CUA capable of being associated with the nonsense amber codon UAG.

Preferably, the mutated cell according to the invention is the *E. coli* cell MG1655 thyA#d2 deposited at the CNCM on Apr. 5$^{th}$ 2007 under number 1-3739.

According to a preferred embodiment, the method according to the invention is characterized in that the gene endA coding for endonuclease 1 comprises a mutation inducing better plasmid stability in said mutated cell. In a more preferred way, the mutated cell according to the invention is the *E. coli* cell MG1655 thyA endA#1.2.C.3 deposited on Apr. 5$^{th}$ 2007 at the CNCM under number I-3738.

According to another preferred embodiment, the method according to the invention is characterized in that the recA gene coding for a recombinase involved in the recombination of DNA sequences is mutated in order to avoid recombination mechanisms between the bacterial genome and the plasmids and between the plasmids. Still more preferably, the mutated cell according to the invention is the *E. coli* cell MG1655 thyA endA recA#TM1a deposited on Apr. 5$^{th}$ 2007 at the CNCM under number I-3737.

According to an advantageous embodiment, the method according to the invention is characterized in that the eukaryotic expression cassette comprises a promoter and polyadenylation sequences, said promoter and said sequences being specific of mammal cells. Preferably, the promoter is the promoter of the cytomegalovirus (CMV) and the polyadenylation sequences are of the "bovine growth hormone" (BGH) type.

According to a particularly advantageous embodiment, the method according to the invention is characterized in that, when the mutated cell is *E. coli*, the suppressor tRNA structural gene sequence is expressed from the strong promoter lpp of the prokaryotic type and contains at its end 3' the termination sequence of the transcription of the operon rrnC, said sequence being preferably oriented in a divergent way relatively to the nucleotide sequence coding for a recombinant protein of interest.

Still more preferably, the method according to the invention is characterized in that said plasmid is the pFAR1 plasmid.

Preferably above all, the method according to the invention is characterized in that said plasmid is the pFAR4 plasmid of sequence SEQ ID NO. 21 or plasmids derived from pFAR4.

Advantageously, the recombinant protein of interest is selected from the group formed by proteins of the eukaryotic type such as those having a therapeutic advantage or those modulating (stimulation/repression) the immune response. Within the scope of DNA vaccination, the protein of interest will belong to the group formed by antigenic determinants identified in pathogens of humans or animals. Preferably, the recombinant protein of interest is selected from the group formed by erythropoietin, dystrophin, insulin, anti-TNFalpha, cytokines, coagulation factors such as the human faction IX, protective antigens such as those from *Bacillus anthracis*, *Mycobacterium tuberculosis* and the prostate specific membrane antigen (PSMA).

According to a fourth aspect, the object of the present invention is a method for producing a recombinant protein of interest comprising:
the multiplication of an expression plasmid according to the multiplication method in accordance with the present invention and described above,
the transformation of the host cell by the expression plasmid obtained in the previous step,
the cultivation of said host cell transformed in a culture medium allowing expression of the recombinant protein of interest, and
the purification of the recombinant protein of interest from the culture medium or from the transformed host cell.

According to a fifth aspect, the object of the present invention is a pharmaceutical composition comprising the expression plasmid according to the invention, the protein of interest of which is selected from the group formed by proteins of the eukaryotic type such as those having either a therapeutic advantage or those modulating (stimulation/repression) the immune response. Within the scope of DNA vaccination, the protein of interest will belong to the group formed by antigenic determinants identified in pathogens of humans or animals and possibly producing toxins. Preferably, the recombinant protein of interest is selected from the group formed by erythropoietin, dystrophin, insulin, anti-TNFalpha, cytokines, coagulation factors such as the human factor IX, protective antigens such as those from *Bacillus anthracis*, *Mycobacterium tuberculosis* and the prostate specific membrane antigen (PSMA).

The expression plasmid may be associated with a chemical and/or biochemical transfection vector. These may notably be cations (calcium phosphate, DEAE-dextran, . . . ), liposomes. The associated synthetic vectors may be cationic polymers or lipids.

The pharmaceutical compositions according to the invention may be formulated with view to administration via a topical, oral, parenteral, intranasal, intravenous, intramuscular, sub-cutaneous, intraocular, transdermal route, etc. Preferably, the expression plasmid is used in an injectable form or as a topical application. It may be mixed with any pharmaceutically acceptable carrier for an injectable formulation, notably for direct injection at the tissue to be treated. These may in particular be sterile, isotonic, solutions. The administration of the plasmid may also be promoted by means of a physical method such as the use of electric fields, electric current, ultrasonic waves, hydrostatic pressure according to the hydrodynamic method. A direct injection into the affected region of the patient is of interest because the therapeutic effect may be concentrated at the affected tissues. As examples of tissues into which the plasmid may be injected, mention may be made of muscle, liver, eye or skin, and also tumors. The doses used may be adapted according to different parameters and notably according to the gene, to the administration method, to the relevant pathology or further to the duration of the treatment.

According to another aspect, the object of the present invention is the use of the expression plasmid according to the invention for in vitro or ex vivo transfection in a host cell of the nucleotide sequence coding for a recombinant protein of interest.

According to another aspect, the object of the present invention is an expression plasmid according to the invention, the recombinant protein of interest of which is selected from the group formed by proteins of the eukaryotic type such as those having a therapeutic advantage or those modulating (stimulation/repression) the immune response, for its use as a drug or as a vaccine. Within the scope of DNA vaccination, the protein of interest will belong to the group formed by antigenic determinants identified in pathogens of humans or animals and possibly producing toxins.

Preferably, the recombinant protein of interest is selected from the group formed by erythropoietin, dystrophin, insulin, anti-TNFalpha, cytokines, coagulation factors such as the human factor IX, protective antigens such as those from *Bacillus anthracis, Mycobacterium tuberculosis* and the prostate specific membrane antigen (PSMA).

The present invention also relates to the use of expression plasmid according to the present invention for the treatment and/or prevention of many pathologies, including genetic diseases, neurodegenerative diseases (Alzheimer, Parkinson, amyotrophic lateral sclerosis, . . . ) cancers, pathologies related to viral infections (AIDS, hepatitises, . . . ). Finally, the present invention relates to a method for treating a pathology such as those mentioned earlier comprising the administration of the expression plasmid according to the present invention to patients in need of such a treatment.

According to a last aspect, the object of the present invention is the use of the expression plasmid according to the present invention or of the mutated cell containing the expression plasmid for producing recombinant proteins of interest.

For practicing the present invention, many standard techniques in molecular biology, microbiology and genetic engineering are used. These techniques are well known and are explained for example, in Current Protocols in Molecular Biology, Volumes 1, 11 and III, 1997 (F. M. Ausubel, ed.); Sambrook et al., 1989, Molecular Cloning; A Laboratory Manual, 2$^{nd}$ edition, Cold Spring Harbor Laboratory Press, Cold Spring Harbor, N.Y.; DNA Cloning; A Practical Approach, Volumes I and II, 1985 (D. N. Glover, ed.); Oligonucleotide Synthesis, 1984 (M. L. Gait, ed.); Nucleic Acid Hybridization, 1985 (Hames et Higgins) Transcription and Translation, 1984 (Hames et Higgins, ed.); Animal Cell Culture, 1986 (R. I. Freshney, ed.); Immobilized Cells and Enzymes, 1986 (IRL Press); Perbal, 1984, A Practical Guide to Molecular Cloning; the series, Methods in Enzymology (Academic Press, Inc.); Gene Transfer Vectors for Mammalian Cells, 1987 (J. H. Miller et M. P. Calos, eds., Cold Spring Harbor Laboratory); et Methods in Enzymology Vol. 154 and Col. 155 (Wu and Grossmann, and Wu, ed. respectively).

The present invention will be more completely described by means of the following examples, which should be considered as illustrative and non-limiting.

FIGURES LEGENDS

Figure 1:
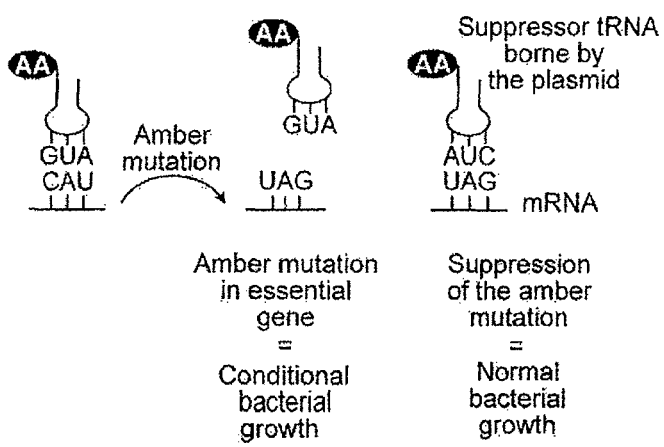

FIG. 1: Descriptive scheme of the strategy used for selecting plasmids without genes for resistance to antibiotics. The introduction of a stop codon of the amber type in the essential gene leads to premature interruption of the synthesis of the protein and to auxotrophy of the mutant. A modification of the anticodon of the tRNA loaded with the preferred amino acid allows pairing of the codon and of the anticodon, the complete synthesis of the protein and the restoration of normal growth of the mutant.

Figure 2:
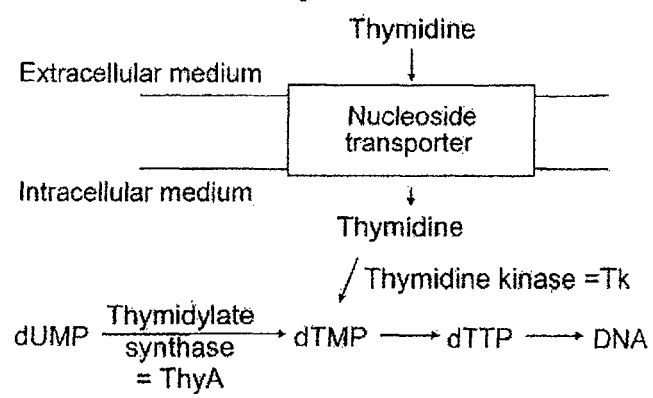

FIG. 2: The mutated essential gene is the thyA gene which codes for thymidylate synthase, an enzyme involved in the synthesis of thymidine monophosphate, which are precursors used during DNA synthesis. A mutation in the thyA gene generates auxotrophy of the mutant for thymidine. The isolation of the mutant is therefore carried out by supplementing the culture medium with thymidine. Exogenous thymidine penetrates into the cell via the nucleoside transporter and is then transformed into dTMP by thymidine kinase.

Figure 3:
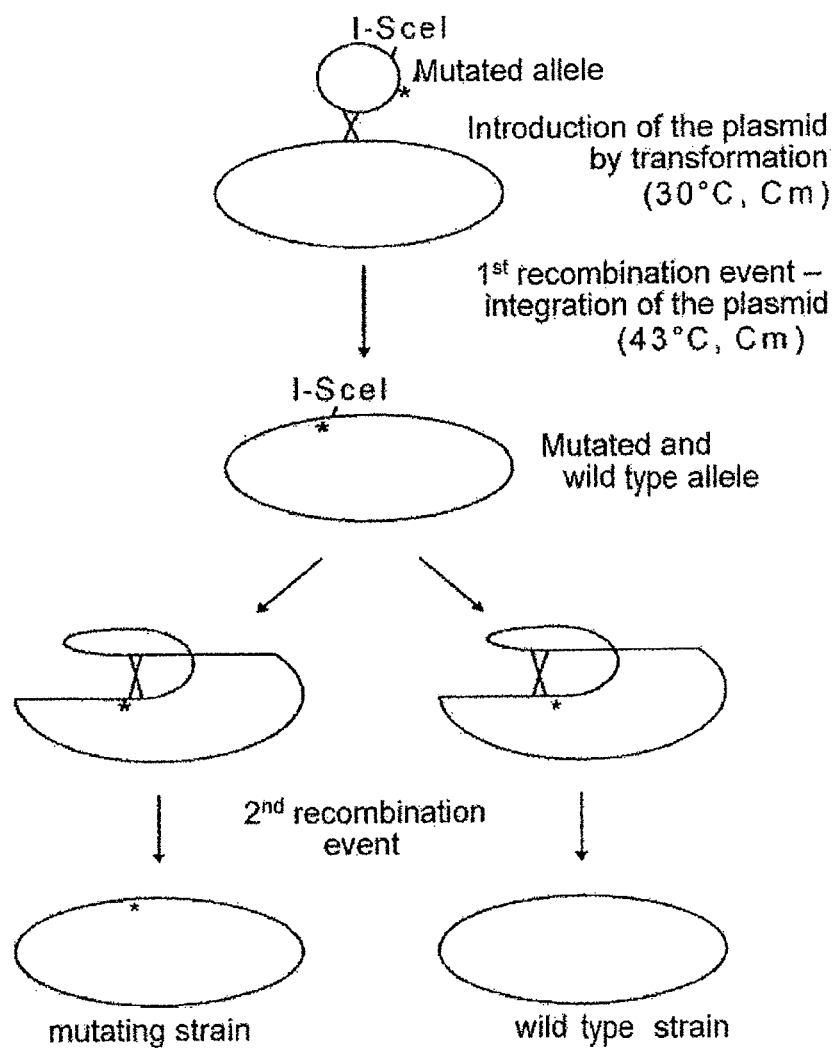

FIG. 3: Construction of bacterial mutants: the insertion of the mutated genes in the genome of *Escherichia coli* is carried out in two steps. The derivatives of the plasmid pST76-C are in a first phase introduced by transformation, by growing the transformants at 30° C. in the presence of chloramphenicol (Cm). The first recombination event leading to the integration of the plasmid is selected by growing the bacteria at 43° C. in the presence of chloramphenicol. A second recombination event will lead to the obtention of a single allele, either mutated or wild. The mutant strains will be screened by carrying out PCRs on colonies.

FIG. 4: Construction of the mutant thyA.

Figure 5:
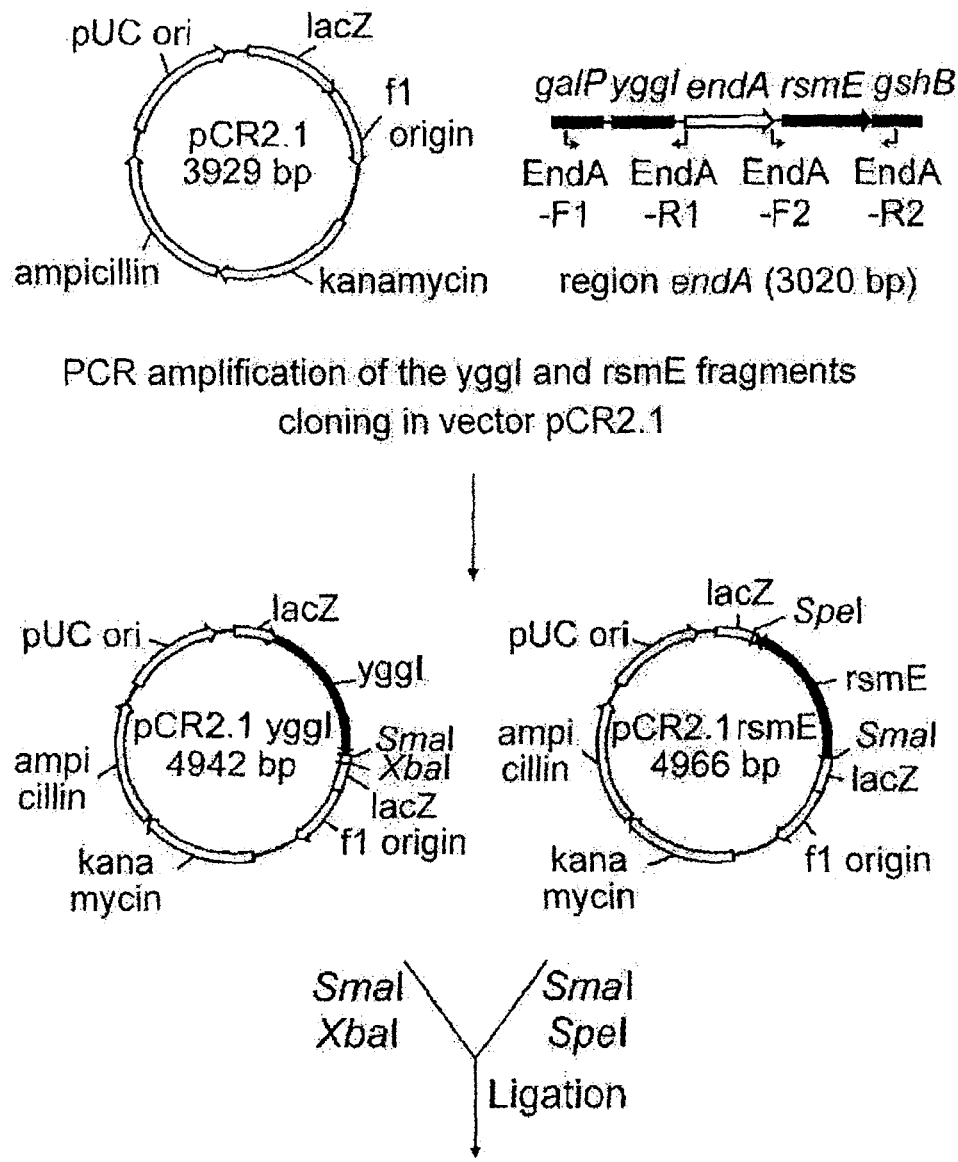
Figure 5:
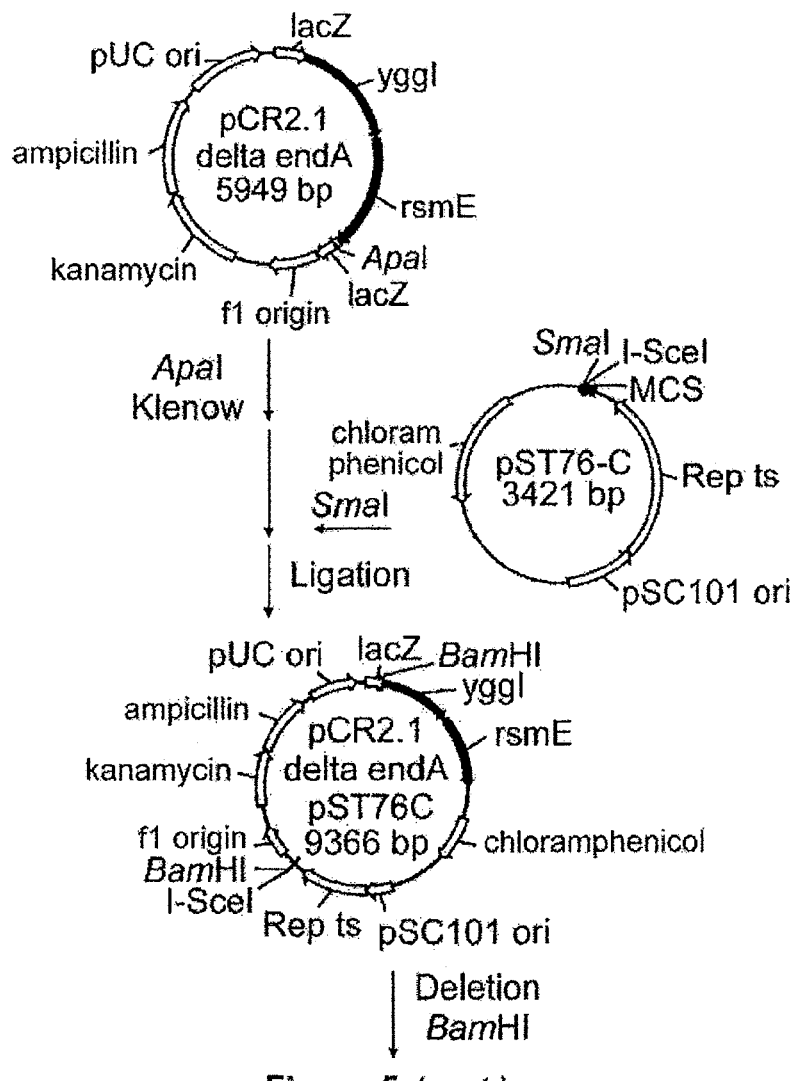

FIG. 5: Construction of the mutant endA.

FIG. 6: Construction of the mutant recA.

FIG. 7: Construction of the plasmids pFAR1 and pFAR1-LUC.

Figure 8:
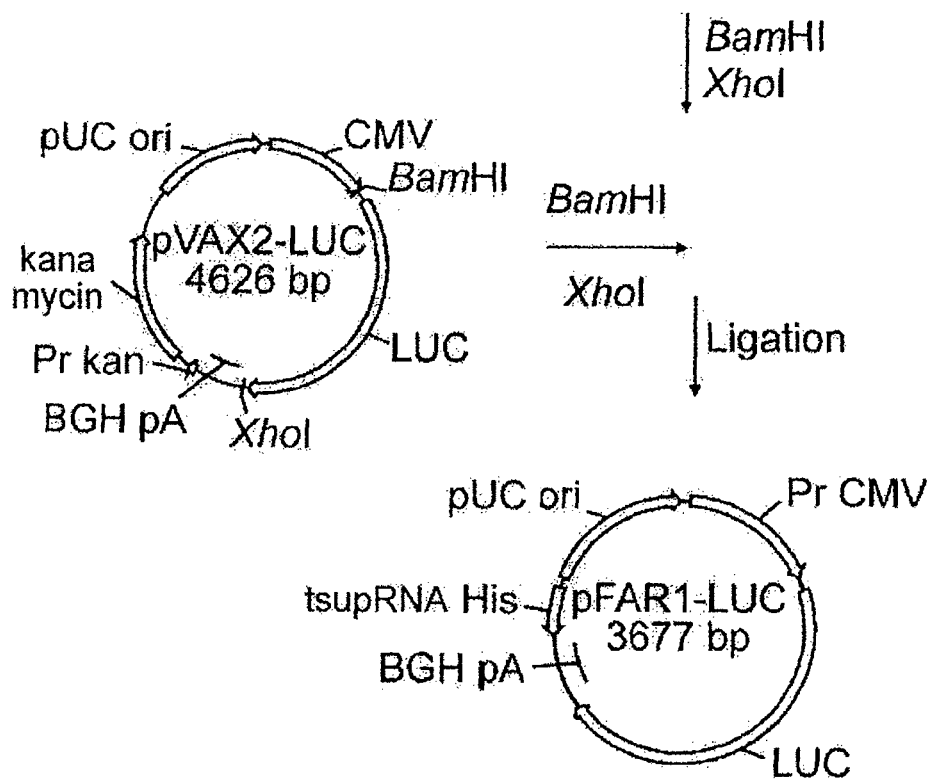
Figure 8:
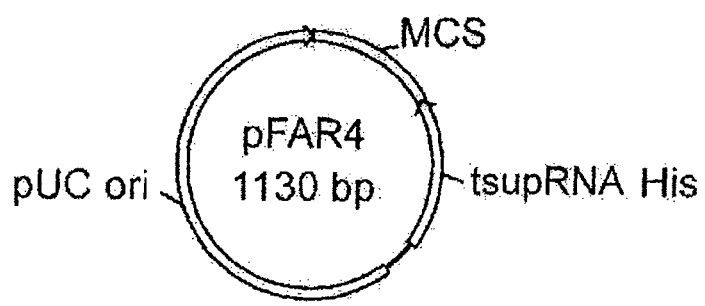

FIG. 8: Map of the plasmid pFAR4: the plasmid pFAR4 is a synthetic plasmid. The MCS (Multiple Cloning Site) sequence contains more than 20 single restriction sites. This plasmid will therefore be used as a backbone vector for constructing a certain number of derivatives containing different types of secretion and eukaryotic expression sequences (ubiquitary or specific promoter of tissues in combination with different polyadenylation sequences).

Figure 9A:
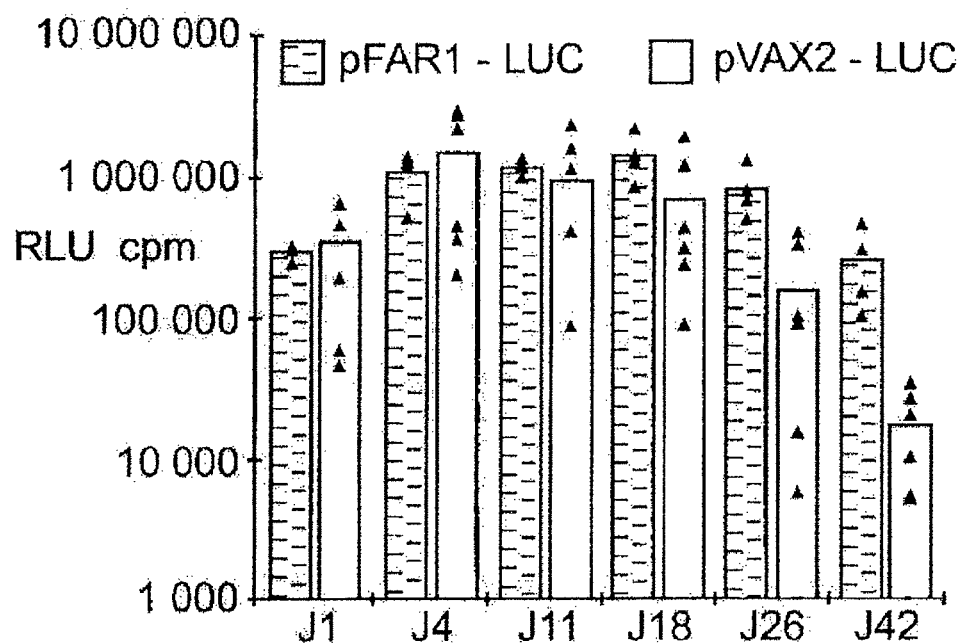
Figure 9B:
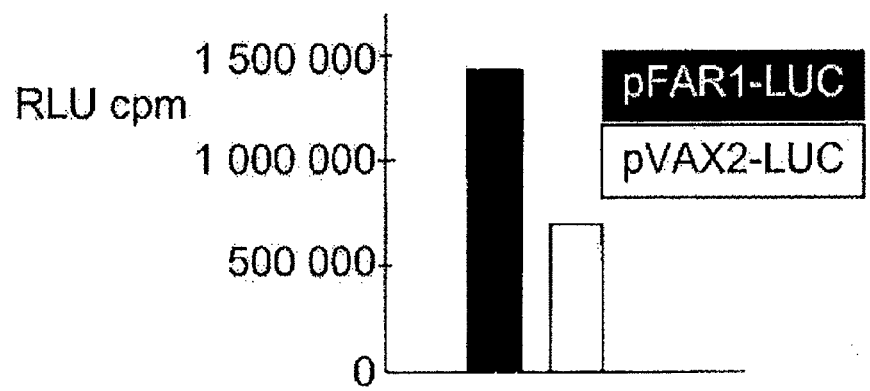

FIG. 9: Quantification of the luciferase activity in murine cranial tibial muscle. At different times after injection of the plasmids pVAX2-LUC and pFAR1-LUC in murine cranial tibial muscle, the substrate of the enzyme, luciferin was administered via an intramuscular route. The enzymatic activity was recorded by using a PhotoImager camera from Bioespaces Mesures. FIG. 9A shows the obtained activities over time on a logarithmic scale. FIG. 9B shows the obtained luciferase activity in a linear representation, 18 days after injecting the plasmids.

Figure 10A:
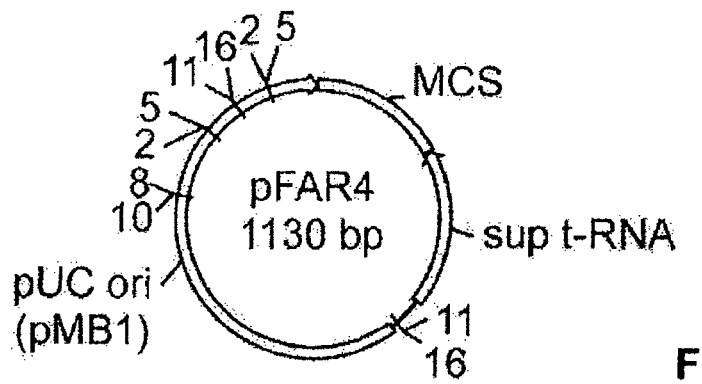

FIG. 10A: Map of the plasmid pFAR4 with viewing of the CpG units.

Figure 10B:
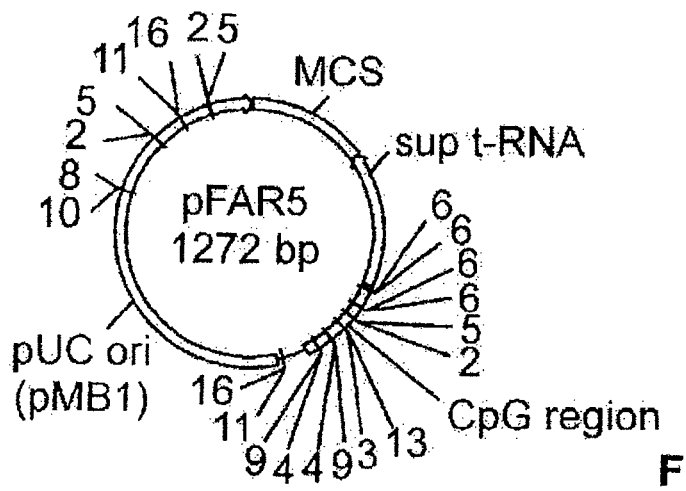

FIG. 10B: Map of the plasmid pFAR5 with viewing of the additional CpG units (CpG region) and of already present CpG units (cf. FIG. 10A).

Figure 10C:
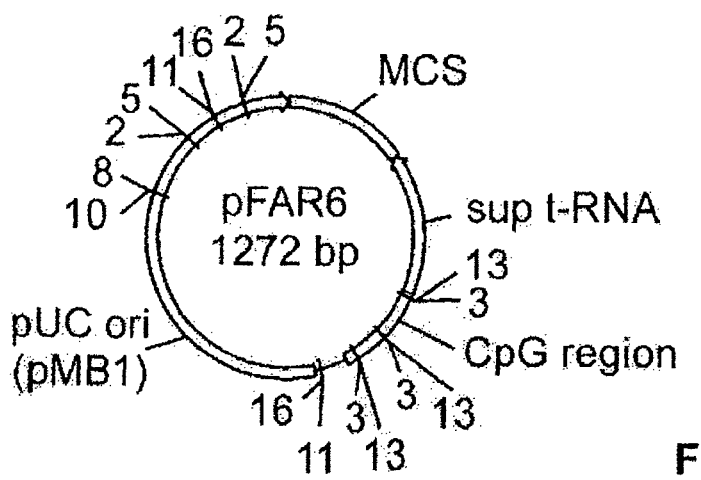

FIG. 10C: Map of the plasmid pFAR6 with viewing of the additional CpG units (CpG region) and of already present CpG units (cf. FIG. 10A).

In FIGS. 10A, 10B and 10C, the numbers 1 to 16 correspond to the different CpG units, present on the two DNA strands, for which the sequences are the following:

1: AACGTT    (SEQ ID NO. 23)

2: AACGCC    (SEQ ID NO. 24)

-continued

| # 3: | AACGTC | (SEQ ID NO. 25) |
| # 4: | AACGCT | (SEQ ID NO. 26) |
| # 5: | GGCGTT | (SEQ ID NO. 27) |
| # 6: | GGCGCC | (SEQ ID NO. 28) |
| # 7: | GGCGTC | (SEQ ID NO. 29) |
| # 8: | GGCGCT | (SEQ ID NO. 30) |
| # 9: | AGCGTT | (SEQ ID NO. 31) |
| # 10: | AGCGCC | (SEQ ID NO. 32) |
| # 11: | AGCGTC | (SEQ ID NO. 33) |
| # 12: | AGCGCT | (SEQ ID NO. 34) |
| # 13: | GACGTT | (SEQ ID NO. 35) |
| # 14: | GACGCC | (SEQ ID NO. 36) |
| # 15: | GACGTC | (SEQ ID NO. 37) |
| # 16: | GACGCT | (SEQ ID NO. 38) |

EXAMPLES

1. Construction of Bacterial Mutants

The mutant thyA was generated from the *Escherichia coli* strain MG1655 (obtained from the "Coli Genetic Stock Center", USA). The genome of this strain has been entirely sequenced (Blattner et al, 1997).

The protocol followed for isolating the *E. coli* mutants is based on the one described by Posfai et al., (1997 and 199). The mutated genes are cloned in a vector, pST76-C, which imparts resistance to chloramphenicol and for which replication is thermosensitive. It is permissive at 30° C. but non-effective between 37 and 43° C. The plasmids are therefore in a first phase introduced into the bacteria by transformation, by selecting the bacteria at 30° C. in the presence of chloramphenicol. In order to select this strain in which the plasmid is integrated after a first recombination event, the bacteria are grown at 43° C. in the presence of chloramphenicol (cf. FIG. 3). The resolution of cointegrates is a rare event in *E. coli* (Posfai et al., 1999). In order to circumvent this problem, the plasmid pST76-ASceP was introduced in the integrants. This plasmid bears a gene coding for a meganuclease, which is an endonuclease which causes double strand breakages at the I-SceI site. The genome of the wild strain MG1655 is without this site. This site is inserted in the bacterial genome after integration of the derivatives of the plasmid pST76-C which has a I-SceI site.

In the presence of meganuclease, only the strains which have lost the I-SceI site, consecutive to intramolecular recombination (cf. FIG. 3), grow. The replication of the plasmid pST76-ASceP is temperature sensitive. It may therefore be easily cured from the mutant strains by growing the bacteria at 43° C.

a. Construction of the thyA Mutant

In order to isolate the mutant strain, a region of 2 kb comprising the thyA gene was amplified by PCR while using the polymerase Ex-Taq (marketed by Takara), from the genomic DNA prepared from the MG1655 strain and the primers ThyA-F and ThyA-R (SEQ ID NOs. 1 and 2) (cf. FIG. 4). These primers were designed so that the mutation is found at the center of the 2 kb fragment. After cloning of the PCR fragment in the vector pCR2.1 (marketed by INVITROGEN) and sequencing, the nonsense mutation of the amber type UAG (TAG) was introduced at the histidine 147. The directed mutagenesis was carried out by using the primers ThyA-His147-F and ThyA-His147-R (SEQ ID NOs. 3 and 4) and the kit QuikChange® II Site-Directed Mutagenesis Kit marketed by Stratagene.

After sequencing the insert in order to check that the 2 kb fragment only contains the desired mutation, the plasmids pCR2.1 region thyA* and pSR76-C (Posfai et al., 1997) were fused after having been digested, by EcoRV and SmaI respectively. In order to eliminate the replication origin pUC ori, the corresponding sequence of the vector pCR2.1 was deleted by digesting the plasmid pCR2.1 region thyA* pSR76-C by BamHI. The mutated fragment thyA fragment is therefore borne by the plasmid pSR76-C region thyA* for which replication is temperature sensitive. This plasmid was introduced by transformation into the MG1655 strain and the first recombination event was then selected by growing the bacteria at 43° C. in the presence of chloramphenicol. The bacterial genome now contains two copies of the thyA gene: a wild-type allele and a mutated allele. The second recombination event was selected by introducing into the integrants the plasmid pST76-SceP which codes for a meganuclease. The strains auxotrophic for thymidine and sensitive to chloramphenicol were selected for analysis. It consists in amplifying by PCR the region containing the gene thyA using the primers ThyA-lgt-FI and ThyA-seq1 (SEQ ID NOs. 5 and 6) and then sequencing the obtained amplicon in order to check that only the gene thyA contains the amber mutation. The thyA mutant was cured of the plasmid pST76-ASceP by growing the strains at 43° C. This was confirmed by checking the loss of resistance to ampicillin conferred by the plasmid pST76A-SceP.

b. Construction of the Dual Mutant thyA-endA

Although the plasmids produced from the thyA mutant grown in a rich medium have purity comparable with that obtained by using other strains, in chemically defined media, the quality of the produced plasmids is inferior. Studies have shown that a mutation in the endA gene, which codes for endonuclease 1, allows this problem to be circumvented (Schoenfeld et al., 1995).

In order to obtain the double mutant thyA-endA, both PCR fragments of 1 kb localized upstream and downstream of the endA gene were amplified with the primers EndA-F1/R1 (SEQ ID NOs. 7 and 8) and EndA-F2/R2 (SEQ ID NOs. 9 and 10), the genomic DNA prepared from the MG1655 strain and the Ex-Taq polymerase (marketed by Takara). These fragments were cloned in the vector pCR2.1 and then sequenced (cf. FIG. 5). The regions located upstream and downstream from the endA gene were fused after digestion of the plasmids pCR2.1 yggI and pCR2.1 rsmE by SmaI/XbaI and SmaI/SpeI, respectively. The plasmid pCR2.1 delta endA was then digested by ApaI, treated by the Klenow fragment, and then ligated to the plasmid pST76-C digested by SmaI. The plasmid pCR2.1 delta endA pST76-C produced was digested by BamHI and then ligated with the purpose of eliminating the replication origin pUC ori. The deleted region of the gene endA was introduced into the genome of the thyA mutant by using a strategy similar to the one described earlier. The mutant strains endA were screened by carrying out PCRs on colonies with the primers EndA-seq1 and EndA-seq5 (SEQ ID NOs. 11 and 12). The obtained PCR fragment was sequenced in order to check whether the integration had occurred at the locus and had not generated any mutation in the genes localized downstream and upstream of the endA gene.

c. Construction of the Triple Mutant thyA-endA-recA

In order to avoid possible recombination mechanisms between the bacterial genome and the plasmids and between the plasmids introduced into the thyA mutant, the recA gene which codes for a recombinase was also deleted. In order to construct the triple mutant thyA-endA-recA, a strategy similar to the one described above was used. PCR fragments localized upstream and downstream of the recA gene were generated by using primers RecA-F1/R1 (SEQ ID NOs. 13 and 14) and RecA-F2/R2 (SEQ ID NOs. 15 and 16), the Ex-Taq polymerase (Takara) and the genomic DNA prepared from the MG1655 strain (cf. FIG. 6). After sequencing of the inserts, the PCR fragments were ligated after digestion of the plasmids pCR2.1 ygaD and pCR2.1 recX by the enzymes SmaI/XbaI and SmaI/SpeI, respectively. The obtained plasmid pCR2.1 delta recA was digested by XBaI, treated with the Klenow fragment, and fused with the plasmid pST76-C digested by SmaI, in order to lead to the formation of the plasmid pCR2.1 delta recA pST76-C. The latter was digested by BamHI and then religated in order to only keep the temperature sensitive replication origin. The mutation was introduced into the bacterial genome by using the same procedure as earlier The selection of the triple mutant was performed by carrying out PCRs on colonies with the primers RecA-seq1 and RecA-R (SEQ ID NOs.17 and 18). The amplicon was sequenced in order to confirm that the integration had been carried out at the locus and that it had not generated any other mutation.

2. Construction of the plasmid pFAR1 (Free of Antibiotic Resistance)

The plasmid pFAR1 was constructed by using the histidine suppressor tRNA in pVAX2 (cf. FIG. 7). pVAX 2 is a derivative of the plasmid pVAX1 (marketed by INVITROGEN) in which the CMV promoter of the plasmid pCMVβ (Clontech) was introduced (Pascal Bigey and Daniel Scherman). The histidine suppressor tRNA is expressed from the strong prokaryotic promoter lpp (Nakamura et al., 1979). In the bacterial genome, this promoter is localized upstream from the gene lpp which codes for a lipoprotein. The end 3' of the suppressor tRNA contains the termination sequence of the transcription of the operon rrnC (Young, 1979). This cassette was amplified from the plasmid pHis (AS) (obtained from "The Coli Genetic Stock Center", USA) by using the primers Nco-sup-F and Nco-sup-Rev (SEQ ID NOs. 19 and 20) and then cloned in the pVAX2 digested by BspHI. The plasmid bearing the suppressor tRNA oriented in a divergent way relatively to the eukaryotic gene was selected in order to eliminate the risk of expression of suppressor tRNA from the eukaryotic promoter CMV in animal cells. The gene imparting resistance to kanamycin was then deleted by digesting the plasmid pVAX2-tsupRNA H is by the enzymes NHindIII (followed by a treatment with the Klenow fragment) and PvuII. This plasmid was designated as pFAR1 (Free of Antibiotic Resistance).

3. Validation of the Strategy

In order to validate the strategy carried out, the plasmid pFAR1 was introduced by transformation into the thyA mutant. The transformants may be selected on any medium free of thymidine. This may be a minimum medium of the M9 type (Sambrook et al., 1989) or a rich medium such as the one of Mueller Hinton (PH). The latter contains meat infusate (2 g/L), casein hydrolysate 17.5 g/L, starch 1.5 g/L and optionally agar-agar. This medium has the advantage of being available commercially (e.g.: from Fluka), of being a rich medium but containing very small or even zero amounts of thymidine. On this medium, the thyA mutant does not develop. On the other hand, the strains containing the pFAR plasmids have a normal growth.

The plasmids pVAX2 and pFAR1 were purified at the same time from the thyA mutant grown in the MH medium. Similar yields were obtained. These results allowed validation of the newly invented combination: an amber mutation in the thyA/ histidine suppressor tRNA gene borne by the plasmid.

4. In Vivo Test of Luciferase Activity

In order to determine whether the plasmids pFAR may be used in vivo, the gene LUC which codes for the luciferase reporter protein was cloned in the plasmid pFAR1. To do this, the plasmid pVAX-LUC was digested by the restriction enzymes BamHI and XhoI and the eukaryotic expression cassette was then cloned in the pFAR1 digested by the same enzymes. 3 μg of pVAX2-LUC and pFAR1-LUC plasmids (in 30 μL of physiological saline) were injected and then electrotransferred into the murine cranial tibial muscle by applying 8 pulses of 20 ms at 200 V/cm, at the frequency of 2 Hz. The substrate of the luciferase, luciferin, was then injected via an intramuscular route at a concentration of 100 μg in a volume of 40 μL. The luciferase activity was recorded at different times after injecting the plasmids by using a PhotoImager camera from Bioespace Mesures (cf. FIG. 9).

These results show that the luciferase activity obtained after injecting the plasmid pFAR1-LUC is similar or even, in certain cases and surprisingly, larger than the one obtained after transfection of the cells by the plasmid pVAX2-LUC. The newly constructed expression vector therefore does not have any disadvantage for in vivo tests, thus giving an additional advantage to the plasmids of the pFAR type.

5. Optimization of the pFAR Plasmids

These promising results led the inventors to optimize the pFAR1 plasmid, with the purpose of reducing its size, of eliminating the maximum of prokaryotic sequences and of introducing single cloning sites which facilitate molecular manipulations. Indeed, prokaryotic sequences are rich in CpG units which may induce inflammatory and immune responses, which should be avoided for gene therapy applications.

The optimized plasmid is called pFAR4 (cf. FIG. 8). The production of this plasmid from the thyA mutant grown in the Mueller Hinton medium has the same properties (yield, purity) as pVAX2.

6. Validation of the Derivatives of pFAR4

Two types of experiments are conducted in order to validate the plasmid pFAR4 for in vivo experiments:

the expression cassette CMV-LUC-BGH is introduced in to the plasmid pFAR4. The plasmids pVAX2-LUC, pFAR1-LUC and pFAR4-CMV LUC BGH are injected into the murine cranial tibial muscle. The luciferase activities are determined at different times after injection and compared. Comparison of the immune response induced after injection of these three plasmids is performed.

the gene coding for murine erythropoietin expressed from the ubiquitous promoter CMV (from the cytomegalovirus) or specific to the MCK (muscle creatine kinase) is cloned in the pFAR4 in order to determine whether this plasmid may also be used in a gene therapy context.

7. Construction of Derivatives of pFAR4

In order to construct a platform of plasmids, the following derivatives of the pFAR4 are constructed (cf. FIG. 8):

pFAR4.1: derivative of pFAR4 containing the ubiquitous CMV promoter (of the cytomegalovirus)

pFAR4.2: derivative of pFAR4 containing the ubiquitous CMV promoter and the BGH polyadenylation sequence pFAR4.3: derivative of pFAR4 containing the ubiquitous CMV promoter and the SV40 polyadenylation sequence pFAR4.4: derivative of pFAR4 containing the specific MCK muscle promoter.

8. Optimization of the pFAR4 Plasmid for DNA Vaccination

Conversely to the application proposed in the previous point 5 (gene therapy—administration of a therapeutic gene), enhanced immune response is desired in the case of vaccination by administration of a DNA coding for an antigen. For this purpose, the inventors have introduced immunostimulating CpG units in the plasmid pFAR4. These CpG units are immunity adjuvants when the plasmid pFAR4 codes for an antigen.

Two derivatives of the plasmid pFAR4, the plasmids pFAR5 (FIG. 10B) and pFAR6 (FIG. 10C) were constructed. They contain different combinations of CpG units.

The plasmid pFAR5 contains on the 5'-3' oriented DNA strand, the 6 following CpG units:

```
2 units GGCGCC,     (SEQ ID NO 28)
1 unit GGCGTT,      (SEQ ID NO 27)
1 unit GACGTT,      (SEQ ID NO 35)
1 unit AGCGTT,      (SEQ ID NO 31)
and
1 unit AACGCT.      (SEQ ID NO 26)
```

These six units are initially those contained in the gene which gives resistance to kanamycin.

The plasmid pFAR6 contains on the 5-3' oriented DNA strand, three times the CpG unit for which the sequence is GACGTT (SEQ ID NO. 35). This sequence represents the optimum unit for immunostimulation in mice (Bauer et al., 2006).

Conclusion

A novel plasmid/*E. coli* mutant strain combination without any genes of resistance to antibiotics was obtained. With the present invention it is possible to select the bacteria transformed by the plasmid of interest by using a rich medium and to obtain a good yield by resorting to standard purification techniques. The minimum medium of type M9 may be used. A rich medium which the inventors have identified is that of Mueller Hinton. It is marketed, inexpensive and does not require a laborious preparation. In vivo, the pFAR1 plasmid does not have any disadvantage as compared with the expression vectors currently used. The inventors observed in certain cases and surprisingly, a stronger expression with the pFAR plasmid than with a plasmid known to one skilled in the art. pFAR1 was optimized and led to the obtaining of the pFAR4 plasmid. After validation and cloning of therapeutic genes or of those coding for antigens, the derivatives of pFAR4 will find many applications in the field of gene therapy, DNA vaccination and the production of recombinant proteins.

List of the Primers Used

Name of the Sequences of the primers (5'-3') Position SEQ ID NO

| Name | Sequence | Position | SEQ ID NO |
|---|---|---|---|
| ThyA-F | CATGCGGTATTGCGCAGGC | 2961939 | 1 |
| ThyA-R | CGCTGTATCTGTTCCGTGTCT | 2963794 | 2 |
| ThyA-His147-F | CGCTGGGACCGTGCTAGGCAT TCTTCCAGTTC | 2962753 | 3 |
| ThyA-His147-R | GAACTGGAAGAATGCCTAGCA CGGTGCCAGCG | 2962722 | 4 |
| ThyA-lgt-FI | GATTCGCGGAGGGTTATAGCG | 2964228 | 5 |
| ThyA-seq1 | GCAGCCAGATTTCATCTTCC | 2961579 | 6 |
| EndA-F1 | GTCGGTTTTGCCATGAGTGC | 3087383 | 7 |
| EndA-R1 | tacccgggTAGACAAATAACG GTACATCAC | 3088387 | 8 |
| EndA-F2 | ttcccgggAGAGCTAACCTAC ACTAGCG | 3089069 | 9 |
| EndA-R2 | CCACTCTTCGTAGTTCTGCT | 3090097 | 10 |
| EndA-seq1 | TGCCACCTTTATCGCAATCG | 3087211 | 11 |
| EndA-seq5 | CTCTTCGGCACGTTCCAGA | 3090220 | 12 |
| RecA-F1 | GTAATGGCAAACGGTCAGGC | 2822782 | 13 |
| RecA-R1 | gatcccgggGTCGATAGCCAT TTTTACTCC | 2821780 | 14 |
| RecA-F2 | catccogggGAAGGCGTAGCAG AAACTAAC | 2820762 | 15 |
| RecA-R2 | GTCGCCGAAGCTGAAGTTG | 2819731 | 16 |
| RecA-seq1 | TATGAAGATGCGTTGAATCG | 2823190 | 17 |
| RecA-R | GGTAACCCACAGACGCTCT | 2819641 | 18 |
| Nco-sup-F | gtccatggCTGGCGCCGCTTCT TTGAGC | | 19 |
| Nco sup-Rev | ccccatggACGACGGCCAGTGC CAAGC | | 20 |

Sequences of the primers used for generating the bacterial mutants or the pFAR plasmids. The number indicated in the last but one column indicates the position of the primers in the genome of the MG1655 strain (accession number: U00096). In order to facilitate the cloning step, restriction sites and additional nucleotides were introduced on the ends of the primers (indicated in lowercase).

BIBLIOGRAPHICAL REFERENCES

Bauer et al., 2001, Human TLR9 confers responsiveness to bacterial DNA via species-specific CpG motif recognition, PNAS, vol. 98, no. 16, 9237-9242.

Blattner et al., 1997. The complete genome sequence of *Escherichia coli* K-12. Science 277: 1453-1474.

Bradley et al., 1981. tRNA$^{Gln}$ Su+2 mutants that increase amber suppression. J. Bacteriol. 145(2): 704-712.

Chaung, 2006, CpG oligodeoxynucleotides as DNA adjuvants in vertebrates and their applications in immunotherapy, International Immunopharmacology 6 (2006), 1586-1596.

Chen et al., 2005. Improved production and purification of minicircle DNA vector free of plasmid bacterial sequences and capable of persistent transgene expression in vivo. Hum. Gene Ther. 16(1):126-131.

Chen et al., 2003. Minicircle DNA vectors devoid of bacterial DNA result in persistent and high-level transgene expression in vivo. Mol. Ther. 8(3):495-500.

Cranenburgh et al., 2004. Effect of plasmid copy number and lac operator sequence on antibiotic-free plasmid selection by operator-repressor titration in *Escherichia coli*. J Mol Microbiol Biotechnol. 7(4): 197-203.

Cranenburgh et al., 2001. *Escherichia coli* strains that allow antibiotic-free plasmid selection and maintenance by repressor titration. Nucleic Acids Res. 29(5):E26

Garmory et al., 2003. DNA vaccines: improving expression of antigens. Genet. Vaccines Ther. I: 2.

Kleina et al., 1990. Construction of *Escherichia coli* amber suppressor tRNA genes. 11. Synthesis of additional tRNA genes and improvement of suppressor efficiency. J. Mol. Biol. 213: 705-717.

Kreiss et al., 1998. Production of a new DNA vehicle for gene transfer using site-specific recombination. Appl. Microbiol. Biotechnol. 49(5):560-567.

Nakamura et al., 1979. DNA sequence of the gene for the outer membrane lipoprotein of *E. coli*: an extremely AT-rich promoter. Cell 18: 1109-1117.

Normanly et al., 1990. Construction of *Escherichia coli* amber suppressor tRNA genes. 111. Determination of tRNA specificity. J. Mol. Biol. 213: 719-726.

Normanly et al., 1986. Construction of two *Escherichia coli* amber suppressor genes: $tRNA^{Phe,CUA}$, and $tRNA^{Cys,CUA}$. Proc. Natl. Acad. Sci. USA. 83: 6548-6552.

Pôsfai et al., 1999. Markerless gene replacement in *Escherichia coli* stimulated by a double-strand break in the chromosome. Nucleic Acid Res. 27: 4409-4415.

Pôsfai et al., 1997. Versatile insertion plasmids for targeted genome manipulations in bacteria: Isolation, deletion, and rescue of the pathogenicity island LEE of the *Escherichia coli* O157:H7 genome. J. Bacteriol. 179(13): 4426-4428.

Sambrook et al., 1989. Molecular cloning. A laboratory manual. Second Edition. Sambrook, Fritsch, Maniatis, Cold Spring Harbor Laboratory Press.

Schoenfeld et al., 1995. Effects of bacterial strains carrying the endA1 genotype on DNA quality isolated with Wizard™ plasmid purification systems. Promega Notes Magazine 53: 12.

Young, 1979. Transcription termination in the *Escherichia coli* ribosomal RNA operon rrnC. J. Biol. Chem. 254(24): 12725-12731.

---

The invention claimed is:

1. An expression plasmid comprising:
   the sequence set forth in SEQ ID NO: 21, and
   an expression cassette comprising a nucleotide sequence coding for a recombinant protein of interest.

2. The expression plasmid of claim 1, wherein the recombinant protein of interest is selected from the group consisting of erythropoietin, dystrophin, insulin, anti-TNFalpha, cytokines, coagulation factors, protective antigens and prostate specific membrane antigen (PSMA).

3. A pharmaceutical composition comprising the expression plasmid of claim 2.

4. The expression plasmid of claim 2, wherein the coagulation factor is human factor IX.

5. The expression plasmid of claim 2, wherein the protective antigens are selected from the group consisting of *Bacillus anthracis* and *Mycobacterium tuberculosis*.

6. A method for producing an expression plasmid as defined in claim 1, said method comprising:
   transforming a mutated *E.coli* cell with the expression plasmid as defined in claim 1; wherein the thyA gene coding for thymidylate synthase of said mutated *E.coli* cell contains a nonsense amber codon UAG, said nonsense codon replacing a codon coding for histidine in position 147 of the thyA gene and leading to interruption of the translation of the thyA gene and auxotrophy of said mutated *E.coli* cell for thymidine,
   growing said transformed mutated *E.coli* cell, and
   extracting the plasmid defined in claim 1 from the cell culture,
   said mutated *E.coli* cell being grown in a medium free of thymidine in order to allow selection of the cell transformed by said plasmid defined in claim 1.

* * * * *

UNITED STATES PATENT AND TRADEMARK OFFICE
CERTIFICATE OF CORRECTION

PATENT NO. : 8,440,455 B2  Page 1 of 1
APPLICATION NO. : 12/675011
DATED : May 14, 2013
INVENTOR(S) : Daniel Scherman and Corinne Marie It is certified that error appears in the above-identified patent and that said Letters Patent is hereby corrected as shown below:

On the Title Page of the Patent

Item (73) Assignees should read as:

--Centre National de la Recherche Scientifique (CNRS), Paris (FR); Universite Paris Descartes, Paris (FR); Institut National de la Sante et de la Recherche Medicale (Inserm), Paris (FR)--.

Signed and Sealed this
Tenth Day of September, 2013

Teresa Stanek Rea
*Acting Director of the United States Patent and Trademark Office*

SEQUENCE LISTING

```
<160> NUMBER OF SEQ ID NOS: 38

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Primer
      ThyA-F

<400> SEQUENCE: 1
catgcggtat tgcgcaggc                                                  19

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Primer
      ThyA-R

<400> SEQUENCE: 2
cgctgtatct gttccgtgtc t                                               21

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Primer
      ThyA-His147-F

<400> SEQUENCE: 3
cgctggcacc gtgctaggca ttcttccagt tc                                   32

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Primer
      ThyA-His147-R

<400> SEQUENCE: 4
gaactggaag aatgcctagc acggtgccag cg                                   32
```

```
<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Primer
      ThyA-lgt-FI

<400> SEQUENCE: 5
gattcgcgga gggttatagc g                                          21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer
      ThyA-seq1

<400> SEQUENCE: 6
gcagccagat ttcatcttcc                                            20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer
      EndA-F1

<400> SEQUENCE: 7
gtcggttttg ccatgagtgc                                            20

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Primer
      EndA-R1

<400> SEQUENCE: 8
tacccgggta gacaaataac ggtacatcac                                 30

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Primer
      EndA-F2

<400> SEQUENCE: 9
ttcccgggag agctaaccta cactagcg                                   28

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer
      EndA-R2

<400> SEQUENCE: 10
ccactcttcg tagttctgct                                            20
```

```
<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer
      EndA-seq1

<400> SEQUENCE: 11
tgccaccttt atcgcaatcg                                                 20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Primer
      EndA-seq5

<400> SEQUENCE: 12
ctcttcggca cgttccaga                                                  19

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Primer
      RecA-F1

<400> SEQUENCE: 13
gtaatggcaa acggtcaggc                                                 20

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Primer
      RecA-R1

<400> SEQUENCE: 14
gatcccgggg tcgatagcca tttttactcc                                      30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Primer
      RecA-F2

<400> SEQUENCE: 15
catcccgggg aaggcgtagc agaaactaac                                      30

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Primer
      RecA-R2

<400> SEQUENCE: 16
gtcgccgaag ctgaagttg                                                  19

<210> SEQ ID NO 17
<211> LENGTH: 20
```

```
<212> TYPE: DNA
<213> ORGANISM: Artificial Sequence
<220> FEATURE:
<223> OTHER INFORMATION: Description of Artificial Sequence: Primer
      RecA-seq1

<400> SEQUENCE: 17
tatgaagatg cgttgaatcg                                              20

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Primer
      RecA-R

<400> SEQUENCE: 18
ggtaacccac agacgctct                                               19

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Primer
      Nco-sup-F

<400> SEQUENCE: 19
gtccatggct ggcgccgctt ctttgagc                                     28

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Primer
      Nco-sup-Rev

<400> SEQUENCE: 20
ccccatggac gacggccagt gccaagc                                      27

<210> SEQ ID NO 21
<211> LENGTH: 1130
<212> TYPE: DNA
<213> ORGANISM: Artificial Sequence
<220> FEATURE:
<223> OTHER INFORMATION: Description of Artificial Sequence: pFAR4
      polynucleotide

<400> SEQUENCE: 21
ggtaccgagc tcttacgcgt gctagcccgg gctcgagatc tgcgatctaa gtaagcttcc    60 gggcccccccc gccatggggt atcgataatg atatcgaatt cctgcagcgg ggatccacta  120
gttctagagc ggccgccacc gcggtggaca gctggctgtc gacgaagtac tgaccggtct  180
taggcctaaa aaaatccttt agctttcgct aaggatctgc agtgggtggg ctaatgggat  240
tcgaacccac gacaactgga tttagaatcc agggctctac caactgagct atagccaccg  300
aattgtgcgt tacaagtatt acacaaagtt ttttatgttg agaatatttt tttgatgggg  360
cgcgacttat ttttgatcgt tcgctcaaag aagcggcgcg tcatgaccaa atcccttaa  420 cgtgagtttt cgttccactg agcgtcagac cccgtagaaa agatcaaagg atcttcttga  480 gatcctttt ttctgcgcgt aatctgctgc ttgcaaacaa aaaaaccacc gctaccagcg  540
gtggtttgtt tgccggatca agagctacca actctttttc cgaaggtaac tggcttcagc  600
```

```
agagcgcaga taccaaatac tgttcttcta gtgtagccgt agttaggcca ccacttcaag    660
aactctgtag caccgcctac atacctcgct ctgctaatcc tgttaccagt ggctgctgcc    720
agtggcgata agtcgtgtct taccgggttg gactcaagac gatagttacc ggataaggcg    780
cagcggtcgg gctgaacggg gggttcgtgc acacagccca gcttggagcg aacgacctac    840
accgaactga gataccctaca gcgtgagcta tgagaaagcg ccacgcttcc cgaagggaga    900
aaggcggaca ggtatccggt aagcggcagg gtcggaacag gagagcgcac gagggagctt    960 ccaggggaa acgcctggta tctttatagt cctgtcgggt ttcgccacct ctgacttgag   1020
cgtcgatttt tgtgatgctc gtcagggggg cggagcctat ggaaaaacgc cagcaacgcg   1080 gccttttac ggttcctggc cttttgctgg ccttttgctc acatgttctt                1130
```

<210> SEQ ID NO 22
<211> LENGTH: 6
<212> TYPE: DNA
<213> ORGANISM: Artificial Sequence
<220> FEATURE:
<223> OTHER INFORMATION: Description of Artificial Sequence:
    Immunostimulant CpG motif
<220> FEATURE:
<221> NAME/KEY: modified_base
<222> LOCATION: (1)..(1)
<223> OTHER INFORMATION: g or a
<220> FEATURE:
<221> NAME/KEY: modified_base
<222> LOCATION: (2)..(2)
<223> OTHER INFORMATION: g or a
<220> FEATURE:
<221> NAME/KEY: modified_base
<222> LOCATION: (5)..(5)
<223> OTHER INFORMATION: t or c
<220> FEATURE:
<221> NAME/KEY: modified_base
<222> LOCATION: (6)..(6)
<223> OTHER INFORMATION: t or c

<400> SEQUENCE: 22 nncgnn                                                                6

<210> SEQ ID NO 23
<211> LENGTH: 6
<212> TYPE: DNA
<213> ORGANISM: Artificial Sequence
<220> FEATURE:
<223> OTHER INFORMATION: Description of Artificial Sequence:
    Immunostimulant CpG motifs 1

<400> SEQUENCE: 23 aacgtt                                                                6

<210> SEQ ID NO 24
<211> LENGTH: 6
<212> TYPE: DNA
<213> ORGANISM: Artificial Sequence
<220> FEATURE:
<223> OTHER INFORMATION: Description of Artificial Sequence:
    Immunostimulant CpG motifs 2

<400> SEQUENCE: 24 aacgcc                                                                6

<210> SEQ ID NO 25
<211> LENGTH: 6
<212> TYPE: DNA
<213> ORGANISM: Artificial Sequence
<220> FEATURE:
<223> OTHER INFORMATION: Description of Artificial Sequence:

-continued

Immunostimulant CpG motifs 3

<400> SEQUENCE: 25 aacgtc                                                                    6

<210> SEQ ID NO 26
<211> LENGTH: 6
<212> TYPE: DNA
<213> ORGANISM: Artificial Sequence
<220> FEATURE:
<223> OTHER INFORMATION: Description of Artificial Sequence:
      Immunostimulant CpG motifs 4

<400> SEQUENCE: 26 aacgct                                                                    6

<210> SEQ ID NO 27
<211> LENGTH: 6
<212> TYPE: DNA
<213> ORGANISM: Artificial Sequence
<220> FEATURE:
<223> OTHER INFORMATION: Description of Artificial Sequence:
      Immunostimulant CpG motifs 5

<400> SEQUENCE: 27 ggcgtt                                                                    6

<210> SEQ ID NO 28
<211> LENGTH: 6
<212> TYPE: DNA
<213> ORGANISM: Artificial Sequence
<220> FEATURE:
<223> OTHER INFORMATION: Description of Artificial Sequence:
      Immunostimulant CpG motifs 6

<400> SEQUENCE: 28 ggcgcc                                                                    6

<210> SEQ ID NO 29
<211> LENGTH: 6
<212> TYPE: DNA
<213> ORGANISM: Artificial Sequence
<220> FEATURE:
<223> OTHER INFORMATION: Description of Artificial Sequence:
      Immunostimulant CpG motifs 7

<400> SEQUENCE: 29 ggcgtc                                                                    6

<210> SEQ ID NO 30
<211> LENGTH: 6
<212> TYPE: DNA
<213> ORGANISM: Artificial Sequence
<220> FEATURE:
<223> OTHER INFORMATION: Description of Artificial Sequence:
      Immunostimulant CpG motifs 8

<400> SEQUENCE: 30 ggcgct                                                                    6

<210> SEQ ID NO 31
<211> LENGTH: 6
<212> TYPE: DNA
<213> ORGANISM: Artificial Sequence
<220> FEATURE:
<223> OTHER INFORMATION: Description of Artificial Sequence:
      Immunostimulant CpG motifs 9

```
<400> SEQUENCE: 31 agcgtt                                                                  6

<210> SEQ ID NO 32
<211> LENGTH: 6
<212> TYPE: DNA
<213> ORGANISM: Artificial Sequence
<220> FEATURE:
<223> OTHER INFORMATION: Description of Artificial Sequence:
      Immunostimulant CpG motifs 10

<400> SEQUENCE: 32 agcgcc                                                                  6

<210> SEQ ID NO 33
<211> LENGTH: 6
<212> TYPE: DNA
<213> ORGANISM: Artificial Sequence
<220> FEATURE:
<223> OTHER INFORMATION: Description of Artificial Sequence:
      Immunostimulant CpG motifs 11

<400> SEQUENCE: 33 agcgtc                                                                  6

<210> SEQ ID NO 34
<211> LENGTH: 6
<212> TYPE: DNA
<213> ORGANISM: Artificial Sequence
<220> FEATURE:
<223> OTHER INFORMATION: Description of Artificial Sequence:
      Immunostimulant CpG motifs 12

<400> SEQUENCE: 34 agcgct                                                                  6

<210> SEQ ID NO 35
<211> LENGTH: 6
<212> TYPE: DNA
<213> ORGANISM: Artificial Sequence
<220> FEATURE:
<223> OTHER INFORMATION: Description of Artificial Sequence:
      Immunostimulant CpG motifs 13

<400> SEQUENCE: 35 gacgtt                                                                  6

<210> SEQ ID NO 36
<211> LENGTH: 6
<212> TYPE: DNA
<213> ORGANISM: Artificial Sequence
<220> FEATURE:
<223> OTHER INFORMATION: Description of Artificial Sequence:
      Immunostimulant CpG motifs 14

<400> SEQUENCE: 36 gacgcc                                                                  6

<210> SEQ ID NO 37
<211> LENGTH: 6
<212> TYPE: DNA
<213> ORGANISM: Artificial Sequence
<220> FEATURE:
<223> OTHER INFORMATION: Description of Artificial Sequence:
      Immunostimulant CpG motifs 15

<400> SEQUENCE: 37
```

```
gacgtc                                                           6

<210> SEQ ID NO 38
<211> LENGTH: 6
<212> TYPE: DNA
<213> ORGANISM: Artificial Sequence
<220> FEATURE:
<223> OTHER INFORMATION: Description of Artificial Sequence:
      Immunostimulants CpG motifs 16

<400> SEQUENCE: 38 gacgct                                                           6
```